(12) United States Patent
Thomas et al.

(10) Patent No.: US 10,794,898 B2
(45) Date of Patent: Oct. 6, 2020

(54) HIGH-THROUGHPUT, HIGH-PRECISION METHODS FOR DETECTING PROTEIN STRUCTURAL CHANGES IN LIVING CELLS

(71) Applicants: REGENTS OF THE UNIVERSITY OF MINNESOTA, Minneapolis, MN (US); LOYOLA UNIVERSITY CHICAGO, Maywood, IL (US)

(72) Inventors: David D. Thomas, Minneapolis, MN (US); Simon Joseph Gruber, Brooklyn, NY (US); Razvan L. Cornea, Saint Paul, MN (US); Gregory David Gillispie, Falcon Heights, MN (US); Kurt C. Peterson, Saint Paul, MN (US); Seth Louis Robia, Westchester, IL (US)

(73) Assignees: Regents of the University of Minnesota, Minneapolis, MN (US); Loyola University Chicago, Maywood, IL (US)

( * ) Notice: Subject to any disclaimer, the term of this patent is extended or adjusted under 35 U.S.C. 154(b) by 0 days.

(21) Appl. No.: 14/598,707

(22) Filed: Jan. 16, 2015

(65) Prior Publication Data
US 2015/0204847 A1 Jul. 23, 2015

Related U.S. Application Data

(60) Provisional application No. 61/928,565, filed on Jan. 17, 2014.

(51) Int. Cl.
| | | |
|---|---|---|
| G01N 33/50 | (2006.01) |
| G01N 21/64 | (2006.01) |
| G01N 33/58 | (2006.01) |

(52) U.S. Cl.
CPC ....... G01N 33/502 (2013.01); G01N 21/6408 (2013.01); G01N 21/6428 (2013.01); G01N 33/582 (2013.01); G01N 2021/6441 (2013.01)

(58) Field of Classification Search
None
See application file for complete search history.

(56) References Cited

U.S. PATENT DOCUMENTS

| 6,816,102 B2 | 11/2004 | Pavicic |
| 7,413,862 B2 | 8/2008 | Van Dongen et al. |
| 2006/0134644 A1 | 6/2006 | Hartel et al. |
| 2012/0021926 A1* | 1/2012 | Thomas ............... G01N 33/542 506/7 |
| 2013/0231262 A1 | 9/2013 | Robia |
| 2015/0204847 A1 | 7/2015 | Thomas et al. |

FOREIGN PATENT DOCUMENTS

WO WO 2010/085514 A1 7/2010

OTHER PUBLICATIONS

Gruber et al.( Biochemical and biophysical research communications 420.2 (2012): 236-240.).*
Pritz et al.(Expert opinion on drug discovery 6.6 (2011): 663-670).*
Cornea et al.(Journal of biomolecular screening 18.1 (2013): 97-107; published online Oct. 24, 2012). (Year: 2012).*
Comley, John. "Fluorescence Lifetime." Drug Discovery (2010): 71-82: 12 pages (Year: 2010).*
Robia et al. (Circulation research101.11 (2007): 1123-1129.) (Year: 2007).*
Poster presentation by Fluorescence Innovations, Inc. ( Lifetime Characterization of Cerulean::Venus FRET Standards in Live Cells Using the NovaFluor PR Fluorescence Lifetime Plate Reader, available online Dec. 8, 2010) (Year: 2010).*
Acker et al., "Considerations for the design and reporting of enzyme assays in high-throughput screening applications," *Perspect Sci*, May 2014;1(1-6):56-73.
Ai et al., "Ca2+/calmodulin-dependent protein kinase modulates cardiac ryanodine receptor phosphorylation and sarcoplasmic reticulum Ca2+ leak in heart failure," *CircRes*, 2005;97:1314-1322.
Andersson et al., Leaky ryanodine receptors in beta-sarcoglycan deficient mice: A potential common defect in muscular dystrophy, *Skelet Muscle*, 2012;2:9.
Aracena et al., "Effects of S-Glutathionylation and S-Nitrosylation on Calmodulin Binding to Triads and FKBP12 Binding to Type 1 Calcium Release Channels," *Antioxid Redox Signal*, 2005;7:870-881.
Arbabian et al., "Endoplasmic reticulum calcium pumps and cancer," *Biofactors*, 2011;37:139-149.
Ariazi et al., "Estrogen-related receptors as emerging targets in cancer and metabolic disorders" *Curr Top Med Chem*, 2006;6:203-215.
Arnou et al., "The Plasmodium falciparum Ca(2+)-ATPase PfATP6: insensitive to artemisinin, but a potential drug target," *Biochem Soc Trans*, 2011;39:823-831.

(Continued)

*Primary Examiner* — Tracy Vivlemore
*Assistant Examiner* — Sahana S Kaup
(74) *Attorney, Agent, or Firm* — Mueting Raasch Group

(57) ABSTRACT

Methods for identifying a compound that alters fluorescence resonance energy transfer (FRET) of a protein. The methods include use of a genetically engineered cell that includes a target protein. The target protein includes one or more heterologous domains. In one embodiment, a target protein includes two heterologous domains, and in another embodiment, the target protein includes a heterologous domain and the cell further includes a second protein that includes a heterologous domain. A heterologous domain may include a chromophore or an amino acid to which a fluorescent dye attaches. The fluorescence lifetime of one or more chromophore, one or more fluorescent dye, or the combination thereof, is measured after contacting the cell with a compound A difference between the fluorescence lifetime in the presence of the test compound and the fluorescence lifetime in the absence of the test compound indicates that the test compound alters the FRET of the target protein.

19 Claims, 15 Drawing Sheets

Specification includes a Sequence Listing.

(56) References Cited

OTHER PUBLICATIONS

Ausubel, R.M., *Current Protocols in Molecular Biology*, 1994.
Bagshaw et al., "ATP analogues at a glance," *J Cell Science*, Feb. 1, 2001;114(3):459-460.
Balog et al., *AmJPhysiolHeartCircPhysiol.*, 2006;290:H794-H799.
Balshaw et al., "Modulation of intracellular calcium-release channels by calmodulin," *J Membr Biol.*, 2002;185:1-8.
Balshaw et al., "Calmodulin Binding and Inhibition of Cardiac Muscle Calcium Release Channel (Ryanodine Receptor)," *JBiolChem*, 2001;276;20144-20153.
Banerjee et al., "Proteoliposome as the model for the study of membrane-bound enzymes and transport proteins," *Molecular and Cellular Biochemistry*, 1983;50:3-15.
Beechem et al., *Numer Comput Methods*, 1992;210;37.
Bers DM, "Cardiac excitation-contraction coupling," *Nature*, 2002;415:198-205.
Bers, "Macromolecular complexes regulating cardiac ryanodine receptor function," *JMolCellCardiol*, 2004;37:417-429.
Bers, "Ryanodine receptor S2808 phosphorylation in heart failure: smoking gun or red herring," *CircRes*, 2012;110:796-799.
Bers DM, "Cardiac Sarcoplasmic Reticulum Calcium Leak: Basis and Roles in Cardiac Dysfunction," *AnnuRevPhysiol*, Feb. 2014;76:107-127.
Bers et al., "Ratio of ryanodine to dihydropyridine receptors in cardiac and skeletal muscle implications for E-C coupling," *Am J Physiol*, 1993;264:C1587-C1593.
Boraso et al., *AmJPhysiol.*, 1994;267:H1010-1016.
Bossuyt et al., "Spatiotemporally Distinct Protein Kinase D Activation in Adult Cardiomyocytes in Response to Phenylephrine and Endothelin," *J Biol Chem*, Sep. 23, 2011;286(38):33390-33400.
Comley, "Fluorescence Lifetime—finally picking up momentum!" Drug Discovery World Summer 2010; pp. 71-82.
Cornea et al., "High-throughput FRET assay yields allosteric SERCA activators," *J Biomol Screen*, Jan. 2013;18(1):97-107.
Cornea et al., "Mapping the ryanodine receptor FK506-binding protein subunit using fluorescence resonance energy transfer," *J BiolChem*, 2010;285:19219-19226.
Cornea et al.,"FRET-based mapping of calmodulin bound to the RyR1 Ca2+ release channel," *PNAS USA*, 2009;106:6128-6133.
Degorce et al., "HTRL: A Technology Tailored for Drug Discovery—A Review of Theoretical Aspects and Recent Applications," *Curr Chem Genomics*, Mar. 2009;3 :22-32.
Diaz-Sylvester et al., "Halothane modulation of skeletal muscle ryanodine receptors: dependence on $Ca^{2+}$, $Mg^{2+}$, and ATP," *AmJPhysiolCellPhysiol.*, Apr. 1, 2008;294(4):C1103-C1112.
Dong et al., "Time-resolved FRET reveals the structural mechanism of SERCA-PLB regulation," *Biochem Biophys Res Commun*, Jun. 27, 2014;449(2):196-201.
Donoso et al., "Stimulation of NOX2 in isolated hearts reversibly sensitizes RyR2 channels to activation by cytoplasmic calcium,"*JMolCellCardiol*, Mar. 2014;68:38-46.
Erickson et al., "A Dynamic Pathway for Calcium-Independent Activation of CaMKII by Methionine Oxidation,"*Cell*, May 2, 2008;133:462-474.
Erickson et al., "Diabetic hyperglycaemia activates CaMKII and arrhythmias by O-linked glycosylation," *Nature*, Oct. 17, 2013; 502:372-376.
Feher et al., "Determinants of calcium loading at steady state in sarcoplasmic reticulum," *Biochem Biophys Acta*, 1983;727:389-402.
Fruen et al., "Differential $Ca^{2+}$ sensitivity of skeletal and cardiac muscle ryanodine receptors in the presence of calmodulin," *Am J Physiol—Cell Phys*, Sep. 1, 2000;279:C724-C733.
Fu et al., "Aberrant lipid metabolism disrupts calcium homeostasis causing liver endoplasmic reticulum stress in obesity," *Nature*, 2011;473:528-531.
Fukuda et al., "Enhanced binding of calmodulin to RyR2 corrects arrhythmogenic channel disorder in CPVT-associated myocytes," *BiochemBiophysResComm*, 2014;448:1-7.

Gakamsky et al., "Use of fluorescence lifetime technology to provide efficient protection from false hits in screening applications," *Anal. Biochem*, Feb. 1, 2011;409(1):89-97.
Gehrig et al., "Hsp72 preserves muscle function and slows progression of sever muscular dystrophy," *Nature*, 2012;484:394-398.
Goonasekera et al., "Mitigation of muscular dystrophy in mice by SERCA overexpression in skeletal muscle," *J Clin Invest*, 2011;121:1044-1052.
Grashoff et al., *Nature(London)*, 2010;466:263.
Greensmith et al., "The effects of hydrogen peroxide on intracellular calcium handling and contractility in the rat ventricular myocyte," *CellCalcium*, 2010;48:341-351.
Gribbon et al., "Fluorescence readouts in HTS: no gain without pain?" *Drug Discov Today*, Nov. 15, 2003;8(22):1035-1043.
Gruber et al., "Phospholamban mutants compete with wild tye for SERCA binding in living cells," *Biochem Biophys Res Commun*, 2012;420:236-240.
Gruber et al., "Discovery of Enzyme Modulators via High-Throughput Time-Resolved FRET in Living Cells," *J Biomolecular Screening*, 2014;19(2):215-222.
Gruber—Presentation—"In-cell FRET as a Tool to Develop SERCA Activators for Drug or Gene Therapy," Poster presented at $57^{th}$ Biophysical Society Annual Meeting, Feb. 2-6, 2013; Philadelphia, PA.
Guo et al., "FRET detection of calmodulin binding to the RyR2 calcium release channel," *BiophysJ*, 2011;101:2170-2177.
Guo et al., "Ca2+/Calmodulin-dependent protein kinase II phosphorylation of ryanodine receptor does affect calcium sparks in mouse ventricular myocytes," *CircRes*, Aug. 18, 2006;99(4):398-406.
Guo et al., "Kinetics of FKBP12.6 binding to ryanodine receptors in permeabilized cardiac myocytes and effects on Ca sparks," *CircRes*, Jun. 11, 2010;106(11):1743-1752.
Hamilton, SL., "Ryanodine receptor structure: Progress and challenges," *J Biol Chem*, Feb. 13, 2009; 284(7):4047-4051.
Hartigan et al., "Tracking HTS Assay Development Time: opportunity for improving drug discovery," Drug Discovery World Summer 2010; pp. 51-58.
Hermanson et al., "Dual mechanisms of sHA 14-1 in inducing cell death through endoplasmic reticulum and mitochondria," *Mol Pharmacol*, 200+9;76:667-678.
Ho et al., *JPhysiol.*, 2011;19:4697-4708.
Hou et al., "2-Color calcium pump reveals closure of the cytoplasmic headpiece with calcium binding," *PLoSONE*, Jul. 11, 2012;7(7):e40369: 10 pgs.
Houser et al., "Protein Kinase A—Mediated Hyperphosphorylation of the Ryanodine Receptor at Serine 2808 Does Not Alter Cardiac Contractility or Cause Heart Failure and Arrhythmias," *CircRes*, Apr. 11, 2014;114(8):1320-1327.
Huang et al., "Two potential calmodulin-binding sequences in the ryanodine receptor contribute to a mobile, intra-subunit calmodulin-binding domain," *J Cell Sci*, Oct. 1, 2013;126(19):4527-4535.
Hwang et al., "Divergent Regulation of Ryanodine Receptor 2 Calcium Release Channels by Arrhythmogenic Human Calmodulin Missense Mutants," *CircRes*, Mar. 28, 2014;114(7):1114-1124.
Ikemoto, "Regulation of calcium release by interdomain interaction within ryanodine receptors," *FrontBiosci*, 2002;7:d671-d683.
Ikemoto, "Ryanodine Receptors: Structure, Function and Dysfunction in Clinical Diseases," New York, NY; Springer, 2004;53-65.
Inesi et al., "The Ca2+ ATPase of ccardiac sarcoplasmic reticulum: Physiological role and relevance to diseases," *Biochem Biophys Res Commun*, 2008;369:182-187.
Inesi et al., "Concerted conformational effects of Ca2+ and ATP are required for activation of sequential reactions in the Ca2+ ATPase (SERCA) catalytic cycle," *Biochemistry*, 2006;45:13769-13778.
Inglese et al., *Nat Chem Biol*, 2007;3:466.
Isenberg et al., *Biophys J*, 1969;9:1337.
Jameson et al., "Investigations of protein—protein interactions using time-resolved fluorescence and phasors," *Methods*, Mar. 1, 2013;59(3):278-286.

(56) References Cited

OTHER PUBLICATIONS

Jessup et al., "Calcium Upregulation by percutaneous Administration of Gene Therapy in Cardiac Disease (CUPID): a phase 2 trial of intracoronary gene therapy of sarcoplasmic reticulum Ca2+-ATPase in patients with advanced heart failure," *Circulation*, 2011;124:304-313.
Johnson et al., "Cardiac sarcoplasimic reticulum function and regulation of contractility-Introduction," *Ann NY Acad Sci*, 1998;853:xi-xvi.
Johnson et al., "Pharmacology of the cardiac sarcoplasmic reticulum calcium ATPase phospholamban interaction," *Ann NY Acad Sci*, 1998;853:380-392.
Jung et al., *EMBOMolMed*, 2012;4:180-191.
Kast et al., *Proc Natl Acad Sci USA*, 2010;107:8207.
Kleinfelder, *Proc SPIE*, 2003;4858:316.
Kimura et al., "Alternative splicing of ryr1 alters the efficacy of skeletal ec coupling," *CellCalcium*, 2009;45:264-274.
Knutson et al., *Chem Phys Lett*, 1983;102:501.
Kobayashi et al., "Dantrolene Stabilzes Domain Interactions within the Ryanodine Receptor," *JBiolChem*, Feb. 25, 2005; 280(8):6580-6587.
Kobayashi et al., "Dantrolene, a therapeutic agent for malignant hyperthermia, markedly improves the function of failing cardiomyocytes by stabilizing interdomain interactions within the ryanodine receptor," *JAmCollCardiol*, 2009;53:1993-2005.
Kobayashi et al., *CircJ.*, 2010;74:2579-2584.
Krause et al., *Anaesthesia*, 2004;59:364-373.
Lagalwar and Orr, *Methods Mol Biol*, 2013;1010:201-209.
Lakowicz et al. *Principles of Fluorescence Spectroscopy*, 3rd ed. Springer, New York, 2006; Table of Contents and Index.
Lebakken et al., "A Fluorescence Lifetime-Based Binding Assay to Characterize Kinase Inhibitors," *J Biomol Screening*, 2007;12:828.
Li et al., *Electrophoresis*, 2014;35(12-13):1846.
Li et al., "A phosphorylation of the ryanodine does not affect calcium sparks in mouse ventricular myocytes," *CircRes*, 2002;90:309-316.
Liu et al., "Dynamic, inter-subunit interactions between the N-terminal and central mutation regions of cardiac ryanodine receptors," *J Cell Sci*, 2010;123:1775-1784.
MacLennan et al., "Phospholamban: a crucial regulator of cardiac contractility," *Nature Reviews*, 2003;4:666-678.
Maltman et al., *Chem Commun*, 2010;46:6929.
Marks, "Calcium cycling proteins and heart failure: Mechanisms and therapeutics," *J Clin Invest*, 2013;123:46-52.
Marquez et al., *Curr Drug Targets*, 2011;12:600-620.
Maruyama et al., "Mutation of aspartic acid-351, lysine-352, and lysine-515 alters the Ca2+ transport activity of the Ca2+-ATPase expressed in COS-1 cells," *PNAS USA*, 1988;85:3314-3318.
Marx et al., *CircRes*, 2001;88:1151-1158.
Maxwell et al., *AmJPhysiolHeartCircPhysiol.*, 2012;302:H953-63.
McMurray et al., *EurHeartJ*, 1993;14:1493-1498.
Meng et al., "Orientation-based FRET sensor for real-time imaging of cellular forces," *J Cell Sci*, 2012;125:743.
Michelangeli et al., "A diversity of SERCA Ca2+ pump inhibitors," *Biochem Soc Trans*, 2011;39:789-797.
Moger et al., *Screening*, 2006;11:765.
Morine et al., "Overexpression of SERCA1a in the mdx diaphragm reduces susceptibility to contraction-induced damage," *Hum Gene Ther*, 2010; 21:1735-1739.
Mueller et al., "SERCA structural dynamics induced by ATP and calcium," *Biochemistry*, 2004;43:12846-12854.
Mueller et al., "Direct detection of phospholamban and sarcoplasmic reticulum Ca-ATPase interaction in membranes using fluorescence resonance energy transfer," *Biochemistry*, 2004;43:8754-8765.
Muretta et al., High-performance time-resolved fluorescence by direct waveform recording, *Rev Sci Instrum*, 2010;81:103101.
Muretta et al., *Proc Acad Natl Sci USA*, 2031;110:7211-7216.
Nesmelov et al., *Proc Acad Nall Sci USA*, 2011;108(5):1891.

Oda et al., "Defective Regulation of interdomain interactions within ryanodine receptor plays a key role in the pathogenesis of heart failure," *Circulation*, 2005;111:3400-3410.
Oda et al., "In Cardiomyocytes, Binding of Unzipping Peptide Activates Ryanodine Receptor 2 and Reciprocally Inhibits Calmodulin binding," *Circulation*, 2013;112:487-497.
Ono et al., *CardiovasRes*, 2010;87:609-617.
Park et al., "Sarco(endo)plasmic reticulum Ca2+-ATPase 2b is a major regulator of endoplasmic reticulum stress and glucose homeostasis in obesity," *Proc Natl Acad Sci USA*, 2010;107:19320-19325.
Paterson et al., "A fluorescence lifetime-based assay for serine and threonine kinases that is suitable for high-throughput screening," *Anal Biochem*, 2010;402:54.
Paul-Pletzer et al., *Biochem J*, 2005;387:905-909.
Peterson et al., "Fluorescence lifetime plate reader: Resolution and precision meet high-throughput," *Review of Scientific Instruments*, 2014;85:113101.
Picht et al., "Sparkmaster: Automated calcium Spark Analysis with ImageJ," *Am J Physiol Cell; Physiol*, :2007;293:C1073-C1081.
Prestle et al., "Overexpression of FK506-binding protein FKBP12.6 in cardiomyocytes reduces ryanodine receptor-mediated Ca(2+) leak from the sarcoplasmic reticulum and increases contractility," *CircRes*, 2001;88:188-194.
Priori et al., "Inherited dysfunction of sarcoplasmic reticulum Ca2+ handling and arrhythmogenesis," *CircRes*, 2011;108:871-883.
Pritz et al., "A Fluorescence Lifetime-Based Assay for Abelson Kinase," *J Biomol Screening*, 2011;16(1): 65-72.
Pritz et al., *Expert Opin Drug Discovery*, 2011;6:663.
Qin et al., *JAmHeartAssoc*, 2013;2:e000184.
Raina et al., *PLoSOne*, 2012;7:e38594.
Rolland et al., "Sarcopenia: Its assessment, etiology, pathogenesis, consequences and future perspectives," *J Nutr Health Aging*, 2008;12:433-450.
Sambrook et al., *Molecular Cloning: A Laboratory Manual*, Cold Spring Harbor Laboratory Press, 1989.
Samsó et al., "Apocalmodulin and Ca2+-calmodulin bind to neighboring locations on the ryanodine receptor," *JBiolChem*, Jan. 11, 2002;277(2):1349-1353.
Samsó et al., "Structural Characterization of the RyR1-FKBP12 interaction," *J Mol Biol*, 2006;356:917-927.
Shan et al., *JClinInvest*, 2010;120:4375-4387.
Simeonov et al., *J Med Chem*, 2008;51:2363.
Song et al., *J Biol Chem*, 2011;286:9120-9126.
Song et al., "Differential integration of Ca2+-calmodulin signal in intact ventricular myocytes at low and high affinity Ca2+-calmodulin targets," *JBiolChem*, 2008;283:31531-31540.
Stange et al., *JBiolChem.*, 2003;278:51693-51702.
Stergiopoulous et al., *BMC Health Serv Res*, 2012;12:345.
Szollosi et al., *CommunicationsinClinicalCytometry*, 1998;34:159-179.
Tateishi et al., "Defective domain-domain interactions within the ryanodine receptor as a critical cause of diastolic $Ca^{2+}$ leak in failing hearts," *CardiovascRes*, 2009;81:536-545.
Tazzeo et al. "the NADPH oxidase inhibitor diphenyleneiodonium is also a potent inhibitor of cholinesterases and the internal Ca(2+) pump," *Br J Pharmacol*, 2009;158:790-796.
Terentyev et al., *CircRes*, 2008;103:1466-1472.
Thomas et al., *PNAS USA*, 1978;75:5746-5750.
Thorne et al., "Apparent activity in high-throughput screening: origins of compound-dependent assay interference," *Curr Opin Chem Biol*, 2010;14:315.
Tung et al., "The amino-terminal disease hotspot of ryanodine receptors forms a cytoplasmic vestibule," *Nature*, 2010;468:585-588.
Uchinoumi et al., "Catecholaminergic polymorphic ventricular tachycardia is caused by mutation-linked defective conformational regulation of the ryanodine receptor," *CircRes*, 2010;106:1413-1424.
Valley et al., "Tumor Necrosis Factor-related Apoptosis-inducing Ligand (TRAIL) Induces Death Receptor 5 Networks That Are Highly Organized," *J Biol Chem*, 2012;287:21265-21278.
Wagner et al., *CircRes*, 2011;108:555-565.

(56) References Cited

OTHER PUBLICATIONS

Wang et al., "Localization of an NH(2)-terminal disease-causing mutation hot spot to the "clamp" region in the three-dimensional structure of the cardiac ryanodine receptor," *JBiolChem*, 2007;282:17785-17793.
Wang et al., *J BiolChem*, 2011;286:12202-12212.
Wehrens et al., "FKBP12.6 deficiency and defective calcium release channel (ryanodine receptor) function linked to exercise-induced sudden cardiac death," *Cell*, 2003;113:829-840.
Wehrens et al., "Ryanodine receptor/calcium release channel PKA phosphorylation: A critical mediator of heart failure progression," *PNAS USA*, 2006;103:511-518.
Xiao et al., "Removal of FKBP12.6 does not alter the conductance and activation of the cardiac ryanodine receptor or the susceptibility to stress-induced ventricular arrhythmias," *J Biol Chem*, 2007;282:34828-34838.
Xu et al., "Defective calmodulin binding to the cardiac ryanodine plays a role in CPVT-associated channel dysfunction," *BiochemBiophysResComm*, 2010;394:660-666.
Yamaguchi et al., "Molecular basis of calmodulin binding to cardiac muscle Ca(2+) release channel (ryanodine receptor)," *J Biol Chem*, 2003;278:23480-23486.
Yamaguchi et al., *JClinInvest*, 2007;117:1344-1353.
Yamamoto et al., "Peptide Probe study of the critical regulatory domain of the cardiac ryanodine receptor," *BiochemBiophysResCommun*, 2002;291:1102-1108.
Yamamoto et al., "Spectroscopic Monitoring of Local Conformational Changes during the Intramolecular Domain-Domain Interaction of the Ryanodine Receptor," *Biochem*, 2002;41(5):1492-1501.
Yamamoto et al., "Postulated role of interdomain interaction within the ryanodine receptor Ca(2+) channel regulation," *JBiolChem*, 2000;275:11618-11625.

Yan et al., "Bidirectional regulation of Ca21 sparks by mitochondria-derived reactive oxygen species in cardiac myocytes," *CardiovasRes*, 2008;77:432-441.
Yang et al., "In situ measurement of RyR2-calmodulin binding in permeablized cardiomyocytes," *Biophys J*, 2011;100:413a-414a.
Yang et al., *CircRes*, 2014;114:295-306.
Yano et al., "Altered stoichiometry of FKBP12.6 versus ryanodine receptor as a cause of abnormal Ca(2+) leak through ryanodine receptor in heart failure," *Circulation*, 2000;2131-2136.
Yano et al., *Circulation*, 2005;112:3633-3643.
Yuan et al., "Genetic mapping of targets mediating differential chemical phenotypes in Plasmodium falciparum," *Nat Chem Biol*, 2009;5:765-771.
Zhang et al., "A simple statistical parameter for use in evaluation and validation of high throughput screening assays," *JBiolScreen*, 1999;4:67-73.
Zima et al., *J Physiol.*, 2010;588:4743-4757.
Simeonov et al., "Fluorescence Spectroscopic Profiling of Compound Libraries," *J Med Chem*, 2008;51:2363.
Fluorescence Innovations, "NovaFluor PR Fluorescence Lifetime Plate Reader" Poster, Mar. 2011.
George, "Ryanodine Receptor Regulation by Intramolecular Interaction between Cytoplasmic and Transmembrane Domains" Jun. 2004 Molecular Biology of the Cell, 15:2627-2638.
Lanner, "Ryanodine Receptors: Structure, Expression, Molecular Details, and Function in Calcium Release" 2010 *Cold Spring Harb Perspectives in Biology*, 2:1-21.
Petegem, "Ryanodine Receptors: Structure and Function" Sep. 2012 *The Journal of Biological Chemistry*, 287(38): 31624-3632.
Gruber, "In cell fret as a tool to develop SERCA activators for drug or gene therapy" poster, 57th Biophysical Society Annual Meeting, Feb. 2-6, 2013. 1 pg.

\* cited by examiner

SEQUENCE LISTING

```
<160> NUMBER OF SEQ ID NOS: 1

<210> SEQ ID NO 1
<211> LENGTH: 6
<212> TYPE: PRT
<213> ORGANISM: artificial
<220> FEATURE:
<223> OTHER INFORMATION: artificial sequence
<220> FEATURE:
<221> NAME/KEY: MISC_FEATURE
<222> LOCATION: (3)..(4)
<223> OTHER INFORMATION: any amino acid

<400> SEQUENCE: 1

Cys Cys Xaa Xaa Cys Cys
1               5
```

HIGH-THROUGHPUT, HIGH-PRECISION METHODS FOR DETECTING PROTEIN STRUCTURAL CHANGES IN LIVING CELLS

CROSS-REFERENCE TO RELATED APPLICATIONS

This application claims the benefit of U.S. Provisional Application Ser. No. 61/928,565, filed Jan. 17, 2014, which is incorporated by reference herein.

GOVERNMENT FUNDING

This invention was made with government support under GM27906, AG42996, and HL092097 awarded by the National Institutes of Health. The government has certain rights in the invention.

SEQUENCE LISTING

This application contains a Sequence Listing electronically submitted via EFS-Web to the United States Patent and Trademark Office as an ASCII text file entitled "2015-03-24-SequenceListing_ST25.txt" having a size of 1 kilobytes and created on Mar. 24, 2015. The information contained in the Sequence Listing is incorporated by reference herein.

BACKGROUND

Fluorescence spectroscopy provides exceptional sensitivity for biological assays, because the fluorescence emission signal is readily separated from excitation and background fluorescence wavelengths, but its precision is limited by the inherent variability of fluorescence intensity. (Gribbon et al., Drug Discov. Today, 8, 1035 (2003); Gakamsky et al., Anal. Biochem., 409, 89 (2011)). Intensity-based measurements are subject to noise due to uncertainty in optical path length or assay volume, light scatter from surfaces or contaminating particulates, differences in local concentration of fluorophores, or presence of interfering fluorescent compounds. (Thorne et al., Curr. Opin. Chem. Biol., 14, 315 (2010).) Nanosecond time-resolved fluorescence measurements provide a way to improve assay resolution and precision because the time-resolved signal is largely independent of intensity variations. (Moger et al. Screening, 11, 765 (2006)). The fluorescence lifetime (an observable related to the quantum yield) may be used to analyze fluorescence decay waveforms by methods including moment analysis, (Isenberg et al., Biophys. J., 9, 1337 (1969)) multi-exponential fitting, (Knutson et al., Chem. Phys. Lett., 102, 501 (1983); Beechem et al., Numer. Comput. Methods, 210, 37 (1992)) or phasor analysis. (Jameson et al., Methods, 59, 278 (2013)). Fluorescence lifetime detection is most useful in assays sensitive to probe environment, such as fluorescence quenching, resonance energy transfer, or intrinsic fluorescence. (Lakowicz, *Principles of Fluorescence Spectroscopy*, 3rd ed. (Springer, New York, 2006)). Lifetime-based assays have been used to measure macromolecular interactions, (Jameson et al., Methods, 59, 278 (2013); Dong et al., Biochem. Biophys. Res. Commun., 449, 196 (2014)) distances, (Kast et al., Proc. Natl. Acad. Sci. U.S.A., 107, 8207 (2010); Muretta et al., Proc. Natl. Acad. Sci. U.S.A., 110, 7211 (2013)) and forces (Grashoff et al., Nature (London), 466, 263 (2010)) as well as enzyme activity and ligand binding. (Lebakken et al., J. Biomol. Screening, 12, 828 (2007); Maltman et al., Chem. Commun., 46, 6929 (2010); Paterson et al., Anal. Biochem., 402, 54 (2010)).

High-precision lifetime measurements are typically performed with time-correlated single-photon counting (TC-SPC), (Becker, *The BH TCSPC Handbook*, 5th ed. (Becker & Hickl, Berlin, 2012)) a digital method that employs low-intensity excitation at the expense of long acquisition times (typically seconds or longer to obtain signal-to-noise≥100). The alternative method of direct waveform recording (DWR) acquires analog fluorescence decays in response to high-intensity pulsed excitation. (Muretta et al., Rev. Sci. Instrum., 81, 103101 (2010)). When using solutions of fluorescent dyes DWR was shown to dramatically reduces acquisition time from ~10 s to ~0.1 ms, without sacrificing accuracy or precision, by exciting many probe molecules with a single pulse and detecting thousands of emitted photons. (Muretta et al., Rev. Sci. Instrum., 81, 103101 (2010)).

SUMMARY OF THE APPLICATION

Described herein are methods for identifying compounds that interact with a target protein, where the interaction alters the structure (conformation) of the target protein. Compounds identified as altering a molecule may be further analyzed to determine if the compound alters a function of the target protein. The methods rely on fluorescence lifetime (FLT) detection of fluorescence resonance energy transfer (FRET) to identify alterations in the target protein, and permit high-throughput screening (HTS), with high precision, of small-molecule libraries for identifying compounds that alter a target protein. As an example of the methods, described herein a two-color SERCA fusion protein was labeled with a fluorescent protein at the N-terminus and a second fluorescent protein inserted into an intramolecular loop. FRET measured between these fluorescent proteins was found to be indicative of SERCA structure, and the assay connects these structural changes with functional activation or inhibition. The two-color molecule was expressed stably in live HEK cells that can be grown in suspension or in adherent culture. Cell fluorescence was read in a microplate using a Fluorescence Lifetime Plate-Reader (FLT-PR). The compounds identified as changing FRET between donor and acceptor are likely to affect SERCA function.

Provided herein are methods for identifying a compound that alters fluorescence resonance energy transfer (FRET) of a protein. In one embodiment, the method includes providing a genetically engineered cell that includes a target protein. In one embodiment, the target protein includes two heterologous domains. The first heterologous domain includes a first chromophore, and the second heterologous domain includes a second chromophore. The method further includes contacting the cell with a test compound to form a mixture, and measuring the fluorescence lifetime of the first chromophore, the second chromophore, or the combination thereof. In one embodiment, the measuring occurs over a period of time no greater than 0.5 seconds, and the coefficient of variation (CV) is no greater than 0.5%. A difference between the fluorescence lifetime in the presence of the test compound and the fluorescence lifetime in the absence of the test compound indicates that the test compound alters the FRET of the target protein. In one embodiment, the fluorescence lifetime of the first chromophore, the second chromophore, or the combination thereof, is changed in the presence of the test compound.

In one embodiment, the target protein includes a heterologous domain, where the heterologous domain includes an amino acid to which a fluorescent dye attaches. The method further includes contacting the cell with a test compound and the fluorescent dye that attaches to the heterologous domain to form a mixture, and measuring the fluorescence lifetime of the fluorescent dye. In one embodiment, the measuring occurs over a period of time no greater than 0.5 seconds, and the coefficient of variation (CV) is no greater than 0.5%. A difference between the fluorescence lifetime in the presence of the test compound and the fluorescence lifetime in the absence of the test compound indicates that the test compound alters the FRET of the target protein. In one embodiment, the fluorescence lifetime of the fluorescent dye is changed in the presence of the test compound.

In one embodiment, a genetically engineered cell includes a target protein and a second protein. The target protein includes a first heterologous domain, and the second protein includes a second heterologous domain, where the first and second heterologous domains are each independently selected from a chromophore and an amino acid to which a fluorescent dye attaches. Thus, the target protein may include a chromophore or an amino acid to which a fluorescent dye attaches, and the second protein may include a chromophore or an amino acid to which a fluorescent dye attaches. The method further includes contacting the cell with a test compound and optionally the fluorescent dye that attaches to the heterologous domain to form a mixture, and measuring fluorescence lifetime of energy emitted by the chromophore, the fluorescent dye, or the combination thereof. In one embodiment, the measuring occurs over a period of time no greater than 0.5 seconds, and the coefficient of variation (CV) is no greater than 0.5%. A difference between the fluorescence lifetime in the presence of the test compound and the fluorescence lifetime in the absence of the test compound indicates that the test compound alters the FRET of the target protein. In one embodiment, the fluorescence lifetime of the chromophore(s), the fluorescent die(s), or the combination thereof, is changed in the presence of the test compound.

The methods may be adapted for use in a high-throughput format. In one embodiment, the cell may be a live cell, where the target protein and optionally the second protein is stably expressed by the genetically engineered cell. In one embodiment, the cell is in suspension. In one embodiment, the cell may be a eukaryotic cell, such as a vertebrate cell. In one embodiment, the measuring may occur over a period of time no greater than 0.001 seconds.

As used herein, the term "protein" refers broadly to a polymer of two or more amino acids joined together by peptide bonds. The term "protein" also includes molecules which contain more than one protein joined by disulfide bonds, ionic bonds, or hydrophobic interactions, or complexes of polypeptides that are joined together, covalently or noncovalently, as multimers (e.g., dimers, tetramers). Thus, the terms peptide, oligopeptide, and polypeptide are all included within the definition of protein and these terms are used interchangeably. It should be understood that these terms do not connote a specific length of a polymer of amino acids, nor are they intended to imply or distinguish whether the protein is produced using recombinant techniques, chemical or enzymatic synthesis, or is naturally occurring.

As used herein, the terms "FRET," "fluorescence resonance energy transfer," "Förster resonance energy transfer" and "resonance energy transfer" are used interchangeably, and refer to a nonradiative energy transfer process that occurs between two chromophores.

As used herein, a "chromophore" is a molecule that includes a region that adsorbs certain wavelengths of light and interacts with such a region of another chromophore so as to be useful for FRET. Chromophores suitable for use in a FRET assay are known to the skilled person and are readily available. In one embodiment, a chromophore may be a donor (also referred to as a donor probe). A donor probe refers to a molecule that will absorb energy and then re-emit at least a portion of the energy over time. In one embodiment, a chromophore may be an acceptor (also referred to as an acceptor probe). An acceptor probe refers to a molecule that will accept energy nonradiatively from a donor, thus decreasing the donor's emission intensity and excited-state lifetime. Thus, provided that a donor probe and an acceptor probe are physically located sufficiently close (most often within 2.5 to 12 nm), the two probes function together and, upon excitation with an appropriate wavelength, the donor probe transfers a precise amount of energy (proportional to the negative sixth power of the donor-acceptor distance) to the acceptor probe. This process can be specifically and quantitatively detected by observing the decrease in donor fluorescence intensity or lifetime or, in some cases, also the energy re-emitted by the acceptor probe as fluorescence. Thus, FRET assays are typically used to measure (1) the mole fraction of donors coupled with acceptor (e.g., to determine the binding affinity between the donor-labeled and acceptor-labeled molecules) and (2) the distance and/or distance changes between donor and acceptor. When donor and acceptor are both attached to the same molecule, FRET can be used to detect a change in the molecule's structure. When donor and acceptor are attached to different molecules, FRET can be used to detect a change in the relative positions (e.g., binding, orientation) and structures of the two molecules. In one embodiment, when a fluorescent dye is attached to a protein, changes in fluorescence of the dye can be used to detect a change in the structure of the protein.

As used herein, the term "high-throughput screening" or "HTS" refers to a method drawing on different technologies and disciplines, for example, optics, chemistry, biology or image analysis, to permit rapid analysis of multiple samples at rates that permit highly parallel biological research and drug discovery.

As used herein, "activity" or "biological activity" of a protein refers to a function of protein in a cell. An activity of a protein in a cell may include binding to another molecule (e.g., an interaction between two subunits of a multimeric protein, or an interaction between a target protein and a non-protein ligand), an enzymatic activity, or the combination thereof.

As used herein, the term "wild-type" refers to the most typical form of an organism, protein, or characteristic as it occurs in nature.

As used herein, "genetically engineered cell" and "genetically modified cell" are used interchangeably and refer to cell into which has been introduced an exogenous polynucleotide and has been altered "by the hand of man." A cell is a genetically engineered cell by virtue of introduction of an exogenous polynucleotide that encodes a target protein described herein. In one embodiment, the genetically engineered cell includes more than one exogenous polynucleotide. In one embodiment, the genetically engineered cell stably expresses a target protein, for instance, the exogenous polynucleotide is not diluted through mitosis and/or degraded (expression of the target protein is not transient).

As used herein, "coefficient of variation" (CV) refers to a normalized measure of dispersion of a probability distribution or frequency distribution, and is defined as the ratio of the standard deviation to the mean.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The description that follows is not intended to describe each disclosed embodiment or every implementation of the present invention. In several places throughout the application, guidance is provided through lists of examples, which can be used in various combinations. In each instance, the recited list serves only as a representative group and should not be interpreted as an exclusive list.

BRIEF DESCRIPTION OF THE FIGURES

FIG. 3. Dose-response effects of known activators and inhibitors on 2CS FRET. Small-molecule SERCA activators developed from our previous SERCA-PLB fluorescence intensity screen both reduce FRET (A and B), and the inhibitor CPA also reduces FRET (C). In all three cases, the concentration dependence of FRET and function are similar.

DETAILED DESCRIPTION OF ILLUSTRATIVE EMBODIMENTS

Figure 1:
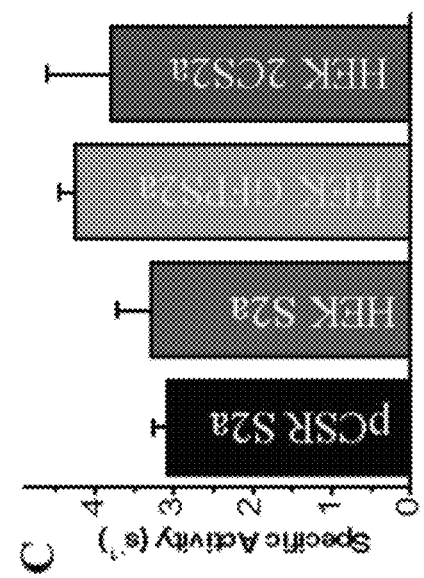
FIG. 1. 2-Color SERCA. (A) Computational model of GFP and RFP modeled on the crystal structure of SERCA1a (PDB 1IWO). (B) Confocal imaging of RFP and GFP (merged) fluorescence with DAPI nuclear stain shows 2-color SERCA localized to intracellular ER membranes. (C) ATPase activity data (mole ATP hydrolyzed per mole of SERCA per second) for pig cardiac SR (pCSR S2a), and stable cell lines expressing unlabeled SERCA2a (HEK S2a), GFP-SERCA2a (HEK GFPS2a), and 2-color-SERCA2a (HEK 2CS2a).
Figure 1:
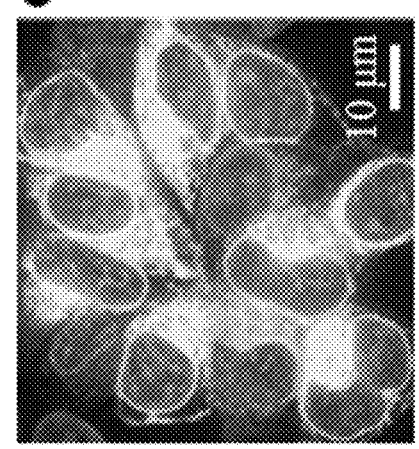
Figure 1:
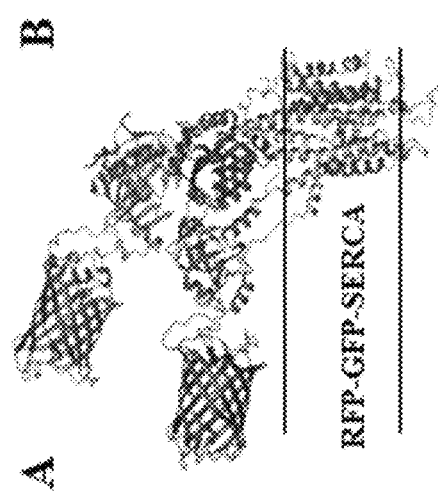

Provided herein are methods for identifying a compound that alters fluorescence resonance emission transfer (FRET) of a target protein. The invention is not limited by the target protein that is used in the method. Examples of suitable target proteins include, but are not limited to, cytoplasmic proteins, membrane-bound proteins, proteins that include one or more transmembrane regions, and nuclear proteins. A target protein used in the methods may be present, for instance, inside a cell, or present on the surface of a cell. A target protein used in the methods may be a subunit of a multimeric protein, where the protein is a homomeric or a heteromeric protein. A target protein may be globular or fibrous. In one embodiment, a target protein is a channel or a pump. In one embodiment, a target protein is associated with the sarcoplasmic reticulum of a cell. Specific examples of target proteins include, but are not limited to, sarco(endo) plasmic reticulum calcium adenosine triphosphatase (SERCA) (Robia, US Patent Application 2013/0231262; Hou et al., 2012, PLoS One, 7:e40369), sodium/potassium ATPase (NKA) (Song et al., 2011, J Biol Chem 286:9120-9126), an ABC transporter MRP1 (Marquez et al., 2011, Curr Drug Targets 12:600-620), a ryanodine receptor (U.S. patent application Ser. No. 14/565,811, Cornea et al.), myosin (Muretta et al., 2013, Proc Natl Acad Sci USA 110:7211-7216), calmodulin kinase II (Erickson et al, 2013, Nature 502:372-376), protein kinase D (Chang et al., 2011, J Biol Chem. 286:33390-33400), ataxin-1 (Lagalwar and Orr, 2013, Methods Mol Biol 1010:201-209), death receptor κ (Valley et al., 2012, J Biol Chem 287:21265-21278), or intermolecular interactions such as SERCA/PLB (Gruber et al., 2012, Biochem and Biophys Comm 420:236-240).

Chromophores suitable for the methods described herein are known to the skilled person and are routinely used. Examples of suitable chromophores include, but are not limited to, fluorescent proteins, including green fluorescent protein, red fluorescent protein, yellow fluorescent protein, and blue fluorescent protein. Green fluorescent protein and red fluorescent protein may be used as a donor-acceptor pair, and blue fluorescent protein and yellow fluorescent protein may be used as a donor-acceptor pair. The amino acid sequences of different version of green fluorescent protein, red fluorescent protein, yellow fluorescent protein, and blue fluorescent protein are known to the skilled person and are readily available, as are analogues of these proteins. Other chromophores include fluorescent dyes, such as fluorescent dyes that can be attached to a protein when the protein is present in a cell. Examples of such dyes are known in the art and are routinely used. Examples include dyes that react with cysteine, having with reactive iodoacetamide, maleimide, or thiosulfonate groups. Other examples include the protein labeling reagent FLASH-EDT2, a dye that can react with the domain CCXXCC (SEQ ID NO:1) (Invitrogen), and SNAP-tag, a self-labeling protein tag (New England Biolabs). Other fluorescent dyes are available that react specifically with an unnatural amino acid that is incorporated into a target protein by a modified tRNA. In one embodiment, a fluorescent dye is one that will pass through a cell membrane.

Any appropriately selected two chromophores can be used as a donor-acceptor pair in the methods described herein, provided that the energy emitted by a donor (the emission spectrum) overlaps with the energy absorbed by an acceptor (the excitation spectrum), e.g., an energy transfer process (FRET) occurs between two chromophores. A donor and an acceptor that meet this overlap are referred to as a donor-acceptor pair. In one embodiment, donor-acceptor pairs are chosen such that interference from cell autofluorescence or test-compound fluorescence is minimized. Accordingly, in one embodiment, donors that can be excited at longer wavelengths are superior to those excitable at shorter wavelengths. Also, probes with longer FLT (more than 3 nanoseconds (ns)) will be superior to probes with shorter FLT.

A target protein used in the methods described herein includes at least one heterologous domain. In one embodiment, a target includes one or two heterologous domains. As used herein, a "heterologous domain" refers to a foreign sequence, e.g., an amino acid sequence that is not normally part of a wild-type protein (e.g., a fluorescent protein, or a domain to which a fluorescent dye can attach such as an amino acid sequence or an unnatural amino acid).

In one embodiment, a target protein includes two heterologous domains, where one of the heterologous domains is a donor probe, and the second is an acceptor probe. In one embodiment, each heterologous domain is a fluorescent protein. In one embodiment, one heterologous domain is a fluorescent protein and the other is a domain to which a fluorescent dye can attach. In one embodiment, each heterologous domain is a domain to which a fluorescent dye can attach. This type of target protein permits analysis of intramolecular FRET.

In one embodiment, a target protein includes one heterologous domain. The heterologous domain may be a donor probe or an acceptor probe. The heterologous domain may be a fluorescent protein or may be a domain to which a fluorescent dye can attach. In one embodiment, the method of using the target protein having one heterologous domain includes fluorescence lifetime analysis of the probe that does not include FRET. In such an embodiment the probe is typically a fluorescent dye that is attached to the target protein, and a change in fluorescence is suggestive of a change in structure. In one embodiment, the method of using the target protein having one heterologous domain includes the use of a second protein. The second protein is also expressed in the cell, and is a protein that binds to the target protein. An example of such protein pairs include SERCA and PLB, and RyR and calmodulin, and many other proteins pairs are known to the skilled person. The second protein is a fusion that contains the second heterologous domain. This type of target protein permits analysis of intermolecular FRET.

In those embodiments where the target protein includes two heterologous domains, each heterologous domain may be present at any location in a target protein. In those embodiments where the target protein includes one heterologous domain and a second protein includes the second heterologous domain, the heterologous domain, whether it is in the target protein or the second protein, may be present at any location in either protein. Thus, a heterologous domain may be at the amino-terminus of a protein, the carboxy-terminus of a protein, or at a location within the protein. However, while the two heterologous domains can be independently located, the two heterologous domains are present at two locations that are close enough to allow FRET to occur between the two. Thus, in one embodiment, a target protein includes a donor probe domain and an acceptor probe domain, where the distance between them in the tertiary structure of the target protein is estimated to be no greater than 2 nanometers (nm), no greater than 4 nm, no greater than 6 nm, no greater than 8 nm, no greater than 10 nm, or no greater than 12 nm. In one embodiment, a target protein includes two heterologous domains, where the distance between them in the primary structure of the target protein is at least 3 amino acids, at least 5 amino acids, at least 10 amino acids, at least 50 amino acids, or at least 100 amino acids. Likewise, in one embodiment, a target protein includes a heterologous domain and a second protein includes a second heterologous domain, where the distance between them in the tertiary structure when the two proteins are bound is estimated to be no greater than 2 nanometers (nm), no greater than 4 nm, no greater than 6 nm, no greater than 8 nm, no greater than 10 nm, or no greater than 12 nm.

In one embodiment, a target protein used in the methods has at least one function in a cell. The role may be related to the mechanical, physical, and/or biochemical function of a cell. For instance, the target protein may bind to another molecule (e.g., an interaction between two subunits of a multimeric protein, an interaction between a target protein and another protein, or an interaction between a target protein and a non-protein ligand), have an enzymatic activity, or a combination thereof. The addition of the two probe domains may alter the function of the target polypeptide in some way. Thus, in one embodiment, the function of a target protein that includes the two probe domains does not have any detectable change. In another embodiment, the function of a target protein that includes the two probe domains does have a detectable change. Target proteins useful in the methods described herein may have altered function, but preserve one or more essential characteristics that can be analyzed as disclosed herein. In some embodiments, a target protein is a wild-type (in other words, it is a wild-type protein modified to include the two heterologous probe domains), and in others the target protein can include one or more mutations associated with altered function of that target protein.

Methods for engineering proteins to include one or more heterologous domains are known in the art and are routine. Typical locations for an inserted heterologous domain include the N-terminus, the C-terminus, and an internal site. Suitable internal sites can be predicted by analysis of a crystal structure of a protein and identification of loop (e.g., not a recognizable helix or sheet) that is exposed to the surface of the protein.

A target protein is expressed in a cell. A polynucleotide sequence encoding the target protein with the two probe domains can be readily produced by reference to the standard genetic code using known and routine methods, and the polynucleotide can be inserted into a vector. A vector is a replicating polynucleotide, such as a plasmid, phage, or cosmid, to which another polynucleotide may be attached so as to bring about the replication of the attached polynucleotide. Construction of vectors containing a polynucleotide encoding a target protein employs standard ligation techniques known in the art. See, e.g., Sambrook et al, *Molecular Cloning: A Laboratory Manual.*, Cold Spring Harbor Laboratory Press (1989) or Ausubel, R. M., ed. *Current Protocols in Molecular Biology* (1994). A vector can provide for further cloning (amplification of the polynucleotide), i.e., a cloning vector, or for expression of the polypeptide encoded by the coding region, i.e., an expression vector. The term vector includes, but is not limited to, plasmid vectors, viral vectors, cosmid vectors, or artificial chromosome vectors.

The cell may be a prokaryotic cell or a eukaryotic cell. Examples of cells useful in the methods described herein include eukaryotic cells and prokaryotic cells. Examples of eukaryotic cells include mammalian cells, such as vertebrate cells, e.g., human, murine (including mouse and rat), canine, or porcine cells. Other examples of eukaryotic cells include invertebrates (such as parasites, including helminths and protozoans such as *Plasmodium* spp.) and unicellular eukaryotic cells, such as yeast cells. Examples of prokaryotic cells include, for instance, *E. coli*. The types of cells useful for expression and analysis of a target protein will vary depending on the target protein, and skilled person will be able to determine which cells can be used based on prior reports of expression of a target protein. For instance, when the target protein is one expressed in muscle cells, such as RyR or SERCA, suitable cells include myocytes, for example ventricular myocytes and cardiomyocytes. In some embodiments, a dysfunctional cell may be used. For example, the cell may be a cancer cell, or myocytes from muscle that is dysfunctional, e.g., failing heart, pathologically stressed, or dystrophic, may be used. In one embodiment, the cell is a cell that can be cultured in suspension (e.g., non-adherent) and does not require contact with a surface for replication. In one embodiment, expression of the target protein in a cell is stable, e.g., an exogenous polynucleotide encoding the target protein is integrated into the genomic DNA of a cell. In one embodiment, the expression of the target protein in a cell is transient.

Methods

In the exemplary methods described herein, the experimental observations indicate that FRET detection of a SERCA protein fused to a red fluorescent protein and a green fluorescent protein provides measurable indications of the structural state of a SERCA molecule in a live cell, which is likely to be related to its function. The methods described herein use the lifetime of a chromophore instead of its intensity. Methods for measuring fluorescence lifetime (FLT) are known to the skilled person and are routine; but the conventional wisdom has been that FLT detection of changes in FRET at high precision was just too slow for high-throughput screening. It was possible to obtain the precision, but the amount of time needed to assay an individual sample was too long for testing libraries of hundreds or thousands of potential drugs. Typical fluorescence lifetime measurements have been used with purified proteins, with reconstituted membranes, or with fluorescent proteins present in cells that were adhered to a surface; all situations where long read times could be done. Prior to conducting the experiments described herein, it was expected that small changes in FRET could not be detected with fluorescence lifetime using the short read times necessary for high-throughput screening. For instance, in a system using purified proteins with reconstituted membranes FRET detection at less than 2 minutes/384-well plate resulted in levels of noise that caused detection of false positives at 72% (Cornea et al., J. Biomol. Screen., 2013, 18, 97-107). This use of purified proteins in a reconstituted system such as that described by Cornea et al. is expected to yield levels of noise that are lower than can be obtained when using living cells. Surprisingly, stable expression in live cells of a target protein fused with a donor probe domain and an acceptor probe domain, coupled with a fluorescence lifetime measurement, resulted in reduced levels of noise and increased precision for detecting subtle protein conformational changes that was 30-fold greater than the precision of fluorescence intensity detection. This precision was even superior to that typically obtained from highly purified proteins labeled with fluorescent donor and acceptor dyes when using fluorescent lifetime measurement. It was surprising and unexpected that analysis of a target protein would work so spectacularly in live cells, which are notorious for variability.

A measuring instrument useful in the methods disclosed herein is a spectrometer that is compatible with FRET assays and can perform direct waveform recording to detect the entire time course of a time-resolved fluorescence decay with high quality (signal/noise>100) within 1 millisecond (ms) or less, in a microplate format that allows for the analysis of at least 100 samples per minute. An example of such an instrument is described by Cornea et al. (*J Biomol Screen*, 2013, 18:97-107). An example of a laser suitable for the methods described herein is a passively Q-switched microchip laser (multi-wavelength series laser devices, model number FP2-473-3-10, manufactured by Concepts Research Corp., Charlotte, N.C., USA). An example of a digitizer suitable for the methods described herein is described in Pavicic (U.S. Pat. No. 6,816,102). An example of direct waveform recording suitable for the methods described herein is described in Muretta, et al. (*Rev Sci Instrum*, 2010, 81:103101).

In one embodiment, FLT is measured using a format that permits rapid evaluation of multiple samples over a short period of time, e.g., a high throughput format. In one embodiment, such a format is a plate reader (FLT-PR). FLT-PRs useful in the methods described herein are readily available (Fluorescence Innovations, Minneapolis, Minn.). The measurement of FLT by using direct waveform recording detection technology in a plate reader provides the precision to resolve small changes in FRET, and can scan the plate rapidly.

Figure 2:
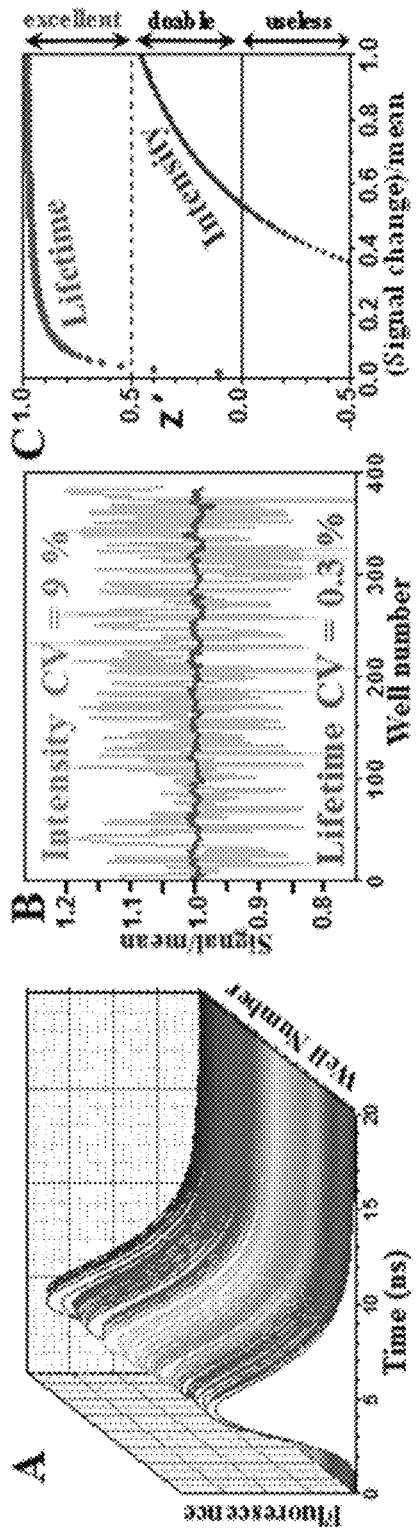
FIG. 2. FLT-PR performance. (A) Waveforms from a high-throughput FRET assay performed in FLT-PR, on live cells expressing 2-color SERCA (identical control samples, no compounds added). (B) Lifetime measurement yields a 30-fold decrease in CV compared with intensity detection. This increased precision greatly decreases the probability of false negatives and positives, thus improving the z' parameter (C) that defines the quality of HTS data (Cornea et al., J Biomol Screen, 2013, 18, 97-107; Michelangeli et al., Biochem Soc Trans 2011, 39, 789-797). Thus even a 1% change in FRET produces excellent HTS quality.

Previously, lifetime plate-readers required a minimum of several hours to scan a 384-well plate at a signal/noise (S/N) of 100 (Muretta, et al., 2010, *Rev Sci Instrum* 81:103101), while a lifetime plate-reader such as those described herein can scan a 384-well plate containing live cells in approximately 2 minutes or less at S/N>100 (Example 1, FIG. 2). The result is a surprising and unexpected improvement in speed by a factor of at least 100. Steady-state fluorescence plate readers (which measure intensity, not lifetime), can operate with similar speed (several minutes per 384-well plate), but they provide much less information and less precision. In Example 1, FIG. 2, Panel A shows FLT decays from all 384 wells (S/N>100) in the FLT-PR. Panel B of FIG. 2 shows differences in variance (CV=StDev/mean %) for fluorescence intensity vs. lifetime (CV=9 vs. 0.3%). The use of FLT-PR improved CV by a factor of 30. The improved CV was surprising and unexpected. The improvement in CV resulted in an excellent quality high-throughput screening index, z', which is routinely used to determine whether an assay is amenable to screening in a high-throughput format. A z'>0.5 indicates an excellent assay that can resolve a given signal change (x-axis). The precision provided by the FLT measurement (FIG. 2C, trace labeled "lifetime") would resolve tiny signal changes (1% or greater), whereas intensity measurement (FIG. 2C, trace labeled "intensity") would typically be useless in high-throughput screening unless signal changes were at least 50%. This is relevant, because the expected magnitude of structural changes that can significantly change the function of a protein includes many changes that are very small (e.g., movement of 5 angstroms or less), resulting in very small changes in FRET (lifetime or intensity changes of 5% or less). Thus, high precision helps to minimize the probability of a false negative—a significant change in the target protein structure that is not detectable by the assay because it is less than the CV. This principle, the need to detect very small structural changes, is especially relevant for the case of enzyme activators, which are likely to act as allosteric effectors (see Example 1). The superior precision of lifetime (FLT) detection, compared to intensity, is largely explained because the FLT readout is much less sensitive to variability in the donor concentration and to sample inhomogeneity (e.g., whether cells or membranes settle at the bottom of the well or are uniformly dispersed throughout the volume of the sample).

In one embodiment, a method includes identifying a compound that alters FRET of a target protein described herein. The method includes providing a genetically engineered cell that includes the target protein, and contacting the cell with a test compound to form a mixture. As described herein, the target protein may have at one or two heterologous domains. In one embodiment, the genetically engineered cell also includes a second protein that contains a heterologous domain. Optionally, in those embodiments where a protein includes a heterologous peptide domain to which a fluorescent dye can attach, the methods further includes contacting the cell with the appropriate protein labeling reagent for labeling the protein with a fluorescent dye. The fluorescence lifetime of the donor probe, the acceptor probe, or a combination thereof is then measured. A difference between the fluorescence lifetime in the presence of the test compound and the fluorescence lifetime in the absence of the test compound indicates that the test compound alters the FRET of the polypeptide. In one embodiment, the alteration of FRET in a target protein may be due to a change in the structure (conformation) of the target. The altered conformation may be a change in the secondary structure, the tertiary structure, or a combination thereof. An alteration in FRET may alter an activity of the target protein, such as an enzymatic activity, or the ability to bind to a ligand, such as an accessory protein. The alteration in FRET is typically at a level that is not detectable when intensity is measured, due to its lower precision. An alteration in FRET may be due to the test compound acting as an activator or an inhibitor of a target protein.

In one embodiment, a method includes identifying a compound that alters the fluorescence lifetime of a fluorescent dye that is attached to a target protein. The method includes providing a genetically engineered cell that includes the target protein that includes a heterologous peptide domain to which a fluorescent dye can attach, contacting the cell with the appropriate protein labeling reagent for labeling the protein with a fluorescent dye, and contacting the cell with a test compound to form a mixture. The fluorescence lifetime of the fluorescent dye is then measured. A difference between the fluorescence lifetime in the presence of the test compound and the fluorescence lifetime in the absence of the test compound suggests that the test compound alters the environment around the fluorescent dye, which in turn suggests the structure (conformation) of the protein has changed in response to the test compound. The altered structure may be a change in the secondary structure, the tertiary structure, or a combination thereof. An alteration in fluorescence lifetime may alter an activity of the target protein, such as an enzymatic activity, or the ability to bind to a ligand, such as an accessory protein. The alteration in fluorescence lifetime is typically at a level that is not detectable when intensity is measured, due to its lower precision. An alteration in fluorescence lifetime may be due to the test compound acting as an activator or an inhibitor of a target protein.

In one embodiment, the genetically modified cell is live. In one embodiment, the genetically modified cell is in suspension. In some embodiments, the conditions used to assay a target protein may be modified to mimic the environment present in a pathological condition. For instance, the target protein may be expressed in a cancer cell, or a cell may be exposed to conditions that mimic a pathological condition. For instance, when using a cardiac cell the cell may be exposed to hypoxic conditions to mimic the conditions present during a myocardial infarction. In one embodiment, the cell may express one or more mutations that mimic a pathological condition. Other conditions vary depending on the type of cell and the type of pathologic condition to be mimicked, and such conditions are known in the art and routinely practiced by the skilled person.

A compound useful in the method includes, but is not limited to, an organic compound, an inorganic compound, a metal, a polypeptide, a non-ribosomal polypeptide, a polyketide, or a peptidomimetic compound. The sources for compounds that may alter activity of a protein described herein include, but are not limited to, chemical compound libraries, fermentation media of *Streptomycetes*, other bacteria and fungi, and cell extracts of plants and other vegetations. Small molecule libraries are available, and include AMRI library, AnalytiCon, BioFocus DPI Library, Chem-X-Infinity, ChemBridge Library, ChemDiv Library, Enamine Library, The Greenpharma Natural Compound Library, Life Chemicals Library, LOPAC1280™, MicroSource Spectrum Collection, Pharmakon, The Prestwick Chemical Library®, SPECS, NIH Clinical Collection, Chiral Centers Diversity Library. In some embodiments, the number of compounds evaluated in an assay includes between 1 and 200,000 compounds, between 1 and 100,000 compounds, between 1 and 1,000 compounds, or between 1 and 100 test compounds.

Measuring the fluorescence lifetime of a donor probe, an acceptor probe, or both, of a cell that includes a single target protein and test compound mixture or a single target protein and second protein and test compound mixture (e.g., a mixture present in a well) may occur over a specific time period. In one embodiment, the time period of measuring the fluorescence lifetime of a mixture is no greater than 5 seconds, no greater than 1 second, no greater than 0.5 seconds, no greater than 0.1 seconds, no greater than 0.01 seconds, no greater than 0.001 seconds, no greater than 0.0001 seconds, no greater than 0.00001 seconds, or no greater than 0.000005 seconds.

In one embodiment, the coefficient of variation (CV) obtained from a sample of cells that include a single target protein and test compound mixture or a single target protein and second protein and test compound mixture (e.g., a mixture present in a well) is no greater than 1%, no greater than 0.5%, or no greater than 0.3%.

In one embodiment, a waveform obtained from a sample of cells that include a single target protein and test compound mixture or a single target protein and second protein and test compound mixture (e.g., a mixture present in a well) has a signal/noise (S/N) that is at least 100, at least 200, at least 300, or at least 400.

In certain embodiments, the FRET assays disclosed herein are measured at a single emission wavelength. In certain embodiments, the FRET fluorescence lifetime properties are measured at two or more wavelengths. In certain embodiments, the methods provided herein are carried out in a well of a plate with a plurality of wells, such as a multi-well plate or a multi-domain multi-well plate. The use of multi-well assay plates allows for the parallel processing and analysis of multiple samples distributed in multiple wells of a plate. Multi-well assay plates (also known as microplates or microtiter plates) can take a variety of forms, sizes and shapes (for instance, round- or flat-bottom multi-well plates). Examples of multi-well plate formats that can be used in the methods provided herein include those found on 96-well plates (12×8 array of wells), 384-well plates (24×16 array of wells), 1536-well plate (48×32 array of well), 3456-well plates and 9600-well plates. Other formats that may be used in the methods provided herein include, but are not limited to, single or multi-well plates comprising a plurality of domains. In certain embodiments, the plates are opaque-wall, opaque-bottom plates. In certain embodiments, the plates are black-wall, black-bottom plates. In certain embodiments, the plates have black walls and clear bottoms in order to allow bottom excitation and reading of the fluorescence signals. In certain embodiments, the plates are chosen with minimal and uniform intrinsic fluorescence intensity within the range used in the method to avoid interference with the FRET signals.

The present invention is illustrated by the following examples. It is to be understood that the particular examples, materials, amounts, and procedures are to be interpreted broadly in accordance with the scope and spirit of the invention as set forth herein.

Example 1

Discovery of Enzyme Modulators Via High-Throughput Time-Resolved FRET in Living Cells A "2-color" SERCA (sarco/endo-plasmic reticulum calcium ATPase) biosensor and a unique high-throughput fluorescence lifetime plate-reader (FLT-PR) was used to develop a high-precision live-cell assay designed to screen for small molecules that perturb SERCA structure. A SERCA construct, in which red fluorescent protein (RFP) was fused to the N terminus and green fluorescent protein (GFP) to an interior loop, was stably expressed in an HEK cell line that grows in monolayer or suspension. Fluorescence resonance energy transfer (FRET) from GFP to RFP was measured in the FLT-PR, which increases precision 30-fold over intensity-based plate-readers without sacrificing throughput. FRET was highly sensitive to known SERCA modulators. A small chemical library was screened and ten compounds that significantly affected 2-color SERCA FLT were identified. Three of these compounds reproducibly lowered FRET and inhibited SERCA in a dose-dependent manner. This assay is ready for large-scale HTS campaigns, and is adaptable to many other targets.

Introduction

Muscle contraction and relaxation are controlled primarily by calcium transport proteins. (Bers, Nature 2002, 415, 198-205). The ryanodine receptor initiates contractions by releasing micromolar levels of $Ca^{2+}$ from the sarcoplasmic reticulum (SR), and relaxation is achieved when the sarcoplasmic reticulum Ca-ATPase (SERCA) pumps $Ca^{2+}$ back into the SR against a 3-log $[Ca^{2+}]$ gradient. In cardiac muscle, the SERCA2a isoform is regulated by the inhibitory transmembrane protein phospholamban, which inhibits $Ca^{2+}$ transport only at low diastolic $[Ca^{2+}]$. SERCA is maximally active at high, systolic $[Ca^{2+}]$ or when PLB is phosphorylated at S16 or T17 by PKA or CaMKII, respectively. PKA phosphorylation of PLB is a key part of the β-adrenergic response pathway activated when cardiac reserves must be accessed. (MacLennan et al., Nature Reviews 2003, 4, 666-678).

Decreased $Ca^{2+}$ transport activity associated with many forms of heart failure (HF) is often due to decreased SERCA2a expression or activity, (MacLennan et al., Nature Reviews 2003, 4, 666-678). so several recent efforts to combat HF aim to correct this dysfunction either by SERCA overexpression (Jessup et al., Circulation 2011, 124, 304-313). or by reducing PLB inhibition. (MacLennan et al., Nature Reviews 2003, 4, 666-678, Gruber et al., Biochem Biophys Res Commun 2012, 420, 236-240). Overexpression of SERCA2a via rAAV gene therapy has been effective in both animal models of HF and human clinical trials. (Jessup et al., Circulation 2011, 124, 304-313). However, the complexities of gene therapy call for a parallel effort to develop small-molecule activators of SERCA. (Banerjee et al., Molecular and Cellular Biochemistry 1983, 50, 3-15.)

Screens for small-molecule SERCA activators have previously focused on directly measuring ATPase activity, which is a low-throughput, low-precision approach. (Johnson et al., Ann N Y Acad Sci 1998, 853, xi-xvi; Johnson et al., Ann N Y Acad Sci 1998, 853, 380-392). We recently reported a FRET-based assay for high-throughput screening of the SERCA-PLB complex in reconstituted membranes. (Banerjee et al., Molecular and Cellular Biochemistry 1983, 50, 3-15.) This HTS assay was designed to detect changes in FRET as an indicator of structural changes caused by compounds that bind to, and structurally alter, the SERCA-PLB complex. A pilot screen was carried out using this method with steady-state (intensity) detection of fluorescence, and hits were resolved, some of which turned out to be SERCA activators. (Cornea et al., J Biomol Screen, 2013, 18, 97-107).

Here, we used a recently developed GFP/RFP "2-color" SERCA2a (2CS) construct as a FRET biosensor (FIG. 1A), (Hou et al., PLoS ONE 2012, 7, e40369). and a fluorescence lifetime plate reader (FLT-PR) to screen, in live cells, for small molecules that affect SERCA structure. The FLT-PR is an instrument constructed in collaboration with Fluorescence Innovations, Inc. (Minneapolis, Minn.), using direct waveform recording, which improves by many orders of magnitude the throughput for high-quality detection of nanosecond time-resolved fluorescence, as needed for precise detection of fluorescence lifetimes. (Muretta et al., Rev Sci Instrum 2010, 81, 103101). The SERCA construct is active and properly localized to intracellular membranes when stably expressed in HEK cells (FIG. 1B,C). GFP-RFP FRET was shown to be sensitive to both $[Ca^{2+}]$ and thapsigargin (TG), a potent SERCA inhibitor, making it an ideal tool to screen for small molecule effectors of SERCA. (Hou et al., PLoS ONE 2012, 7, e40369). We evaluated 2CS FRET in intact live cells in the presence of a variety of previously identified SERCA activators and inhibitors, (Cornea et al., J Biomol Screen, 2013, 18, 97-107). and found that live-cell 2CS FRET is sensitive to SERCA effectors in a dose-responsive manner. We then performed a pilot screen of the 1280-compound Library of Pharmacologically Active Compounds (denoted LOPAC; Sigma-Aldrich) using the live-cell 2CS FRET assay. This screen yielded a few hits, i.e., compounds that significantly changed FRET. Secondary assays, measuring the Ca-ATPase activity, revealed that several hits from the FRET assay also altered SERCA function. This in-cell FRET assay represents a novel, highly sensitive tool to detect both activators and inhibitors of SERCA. The high-precision afforded by direct waveform recording technology implemented in the fluorescence lifetime plate reader (FLT-PR) enables in-cell high-throughput screening (HTS) using 2CS.

Molecular Biology, Cell Culture, and Localization.

Using recombinant DNA technology, the gene for TagRFP was fused to the N-terminus of canine SERCA2a. This fusion position is in the A-domain of the pump. EGFP was fused as an intrasequence tag before residue 509 in the N-domain. The structural model presented in FIG. 1A corresponds to the isoform SERCA1a, which is 84% homologous to SERCA2a. Hou et al. evaluated several intrasequence fusion positions chosen using x-ray crystal structures of SERCA1a to identify unstructured loops and predict large relative distance changes without affecting SERCA function. (Hou et al., PLoS ONE 2012, 7, e40369). The 509 site was chosen because the labeled construct had normal SERCA activity and its intramolecular FRET signal was sensitive to SERCA structural state, as shown below.

Cells were transiently transfected using 293fectin (Invitrogen), and stable cell lines were generated by G418 (Sigma) selection. Surviving clones expressing GFP-SERCA2a or 2CS were further selected by fluorescence microscopy and flow cytometry. Cell lines with the smallest population of non-expressing cells were selected and have been grown continuously while stably expressing 2CS or GFP-SERCA2a for over a year.

Fluorescence microscopy of HEK-GnTI− cells (ATCC, Manassas, Va.) expressing 2CS was performed in glass-bottom chambered coverslips (Matek Corporation, Ashland, Mass.) several weeks after establishing a stable cell line. Confocal microscopy was performed using a Zeiss cell observer SD spinning disk confocal microscope equipped with a 0.55 N.A. 63× oil immersion objective. Cells were stained 20 min before imaging with Hoechst 33342 NucBlue counterstain (Invitrogen) Excitation was accomplished with laser illumination at 405 nm for NucBlue, 488 nm for GFP, and 561 nm for RFP.

Homogenization of Cells for Activity Assays.

Cells were homogenized as previously described. (Maruyama et al., Proc Natl Acad Sci USA 1988, 85, 3314-3318). Briefly, cells were pelleted by spinning at 500 g and washed 3× with PBS. Pellets were resuspended in 1-2 mL homogenization buffer (0.5 mM $MgCl_2$, 10 mM Tris-HCl, pH 7.5, 4° C.) and homogenized with 30 strokes in a Potter-Elvehjem homogenizer. Sucrose buffer (500 mM sucrose, 100 mM MOPS, pH 7.0, 4° C.) was added at a 1:1 ratio and homogenate was assayed for protein concentration (BCA kit from Thermo Scientific, Rockford, Ill.) before flash freezing and storing at −80° C.

Cardiac SR and Skeletal SR Preparation.

Cardiac sarcoplasmic reticulum (SR) vesicles were prepared from the ventricular tissue of swine hearts by adapting a previous method. (Feher et al., Biochim Biophys Acta 1983, 727, 389-402). The heart was placed in a solution (10 mM $NaHCO_3$, 10 mM Tris-HCl, 0.1 mg/mL Aprotinin, 0.1 mg/mL Leupeptin, 80 mM Benzamidine, 100 mM PMSF, 0.1 mg/mL Pepstatin A, pH 7.2, 4° C.) immediately after being sacrificed, and kept on ice. All following procedures were performed at 4° C. The atria, fat and connective tissue were removed from the heart. The ventricular muscles were minced into 1 cm³ pieces and homogenized in 500 mL of SR buffer (100 mM KCl, 20 mM MOPS, pH 7.0, 4° C.) using a blender (Waring, Torrington, Conn.). The homogenates were centrifuged at 5000 rpm (Sorvall, GSA rotor) for 20 minutes. The pellets were collected and treated with homogenization and centrifugation like before. Two supernatants were combined, filtered through 6 layers of cheesecloth, and spun at 8500 rpm (Sorvall, GSA rotor) for 20 min. The supernatant was filtered through 6 layers of cheesecloth. KCl was added to the filtrate to a final 600 mM, and stirred for 15 minutes. The filtrated was spun at 12000 rpm for 1 hour. The pellet was homogenized in 100 mL sucrose buffer (0.1 M sucrose, 1 mM NaN3, 20 mM MOPS, pH 7.0 4° C.), and spun at 30000 rpm (Beckman Ti45 rotor) for 45 minutes. The pellet was homogenized in 15 mL sucrose buffer with a Potter-Elvehjem homogenizer. Total SERCA by weight in these vesicles was 30±5% as determined by densitometry analysis of SDS-PAGE. Rabbit light skeletal SR vesicles were prepared using a method previously reported. (Mueller et al., *Biochemistry* 2004, 43, 12846-12854). Rabbit muscles were harvested from the hind leg of New Zealand White rabbits and purified using a sucrose gradient. The result light skeletal SR contains 80% SERCA.

Enzymatic Activity of 2CS and Compound Effects on Pig Cardiac SR.

An enzyme-coupled, NADH-linked ATPase assay was used to measure SERCA ATPase activity (Stergiopoulos et al., *BMC Health Serv Res* 2012, 12, 345). in 96-well microplates. Each well contained 50 mM MOPS (pH 7.0), 100 mM KCl, 5 mM $MgCl_2$, 1 mM EGTA, 0.2 mM NADH, 1 mM phosphoenol pyruvate, 10 IU/mL of pyruvate kinase, 10 IU/mL of lactate dehydrogenase, 3.5 µg/mL of the calcium ionophore A23187, and $CaCl_2$ added to set free $[Ca^{2+}]$ to the desired values. (Mueller et al., *Biochemistry* 2004, 43, 8754-8765). 2.5 µg of cardiac SR or 25 µg of HEK cell homogenate were used in each well to correct for the difference in SERCA content. The assay was started upon the addition of ATP at a final concentration of 5 mM and read in a SpectraMax Plus microplate spectrophotometer (Molecular Devices, Sunnyvale, Calif.), bring the total volume to 200 µL. Results were normalized to SERCA content determined from immunoblotting.

Effects of known activators and LOPAC hits on SERCA ATPase activity was evaluated in pig cardiac SR. Compounds were dissolved in DMSO, and adjusted to 40 times the concentrations used in the final assay wells. 4 µL prediluted compounds were added to each well to keep the final [DMSO] at 2% (v/v).

Western Blot to Quantify SERCA Content.

Cell homogenates and cardiac SR were subjected to SDS-PAGE on 4-20% Tris-HCl gels (Criterion, Biorad) at 5 µg total protein, transferred to Immobilon-FL membranes (Millipore), and blocked by dipping in methanol and air drying. The membrane was incubated with SERCA2a primary antibody diluted 1:1000 (2A7-A1, Abcam) for 3 h, washed, and visualized by 1 h incubation with goat-anti-mouse 800 nm IR secondary antibody (LI-COR Biosciences). Blots were quantified on the Odyssey scanner (LI-COR Biosciences).

Compound Plating and Fluorescence Lifetime Measurements in Plate Reader.

The 96-well plate format LOPAC library was reformatted into four 384-well polystyrene mother plates (Corning, Corning, N.Y.) using a Biomek FX liquid handler (Beckman Coulter, Brea, Calif.), and diluted to 500 µM using DMSO. Column 1, 22, 23 and 24 were loaded with DMSO for in-plate no-compound controls. The LOPAC compounds were distributed in column 2 through 21. Each plate contains 64 wells of DMSO controls, and 320 wells of compounds from the LOPAC library. Black well, high-quality-glass bottom Greiner 384-well microplates (PN 781892) were selected as the assay plates for their optical clarity, low autofluorescence, and low inter-well cross-talks. Compounds (1 µL) were transferred from the mother plates into assay plates using a Mosquito HV liquid handler (TTP Labtech Ltd, UK). The plates were sealed and stored at −20° C. until use. On the day of screening, the plates were equilibrated to room temperature (25° C.). Stable GFP-SERCA2a (donor only control) or 2CS cells were lifted from a 225 cm² flask by incubating with TrypLE (Invitrogen) for 5 min. Cells were collected and pelleted for 5 min at 500 g and resuspended in 10 mL PBS, then analyzed on a Countess cell counter (Invitrogen) and diluted to 1×10⁶ cells/mL. 49 µL Cells were plated on top of the compounds by a FlexDrop IV reagent dispenser (PerkinElmer, Waltham, Mass.). Assay plates were spun for 1 min at 200 g and allowed to incubate at RT for 20 min before reading on a fluorescence lifetime plate reader (constructed in collaboration with Fluorescence Innovations, Inc., Minneapolis, Minn.). GFP fluorescence was excited with a 473 nm microchip laser from Concepts Research Corporation (Belgium, Wis.) and emission was filtered with 490 nm long pass and 520/35 nm band pass filters from Semrock (Rochester, N.Y.).

HTS Data Analysis.

Time-resolved fluorescence waveforms for each well were fitted to single-exponential decays using global analysis software. Each plate contained 64 control wells with only DMSO, and a hit was defined as a compound that changed the 2CS donor lifetime by more than three times the standard deviation (SD) relative to the controls. Fluorescent compounds that caused the intensity of both untransfected HEK cells and 2CS cells to be more than 3SD outside the mean of the 64 controls on a plate were excluded from the hits as likely false positives.

Results

Ca-ATPase Activity of 2CS.

We have previously reported that a 2CS construct with an N-terminal cerulean and internal yellow fluorescent protein, transiently expressed in HEK cells, actively transports $Ca^{2+}$ and has normal $Ca^{2+}$-dependent ATPase activity. (Hou et al., *PLoS ONE* 2012, 7, e40369). Here, we show that SERCA ATPase activity is not significantly affected by the RFP or GFP probes in stable cell lines (FIG. 1C). Both unlabeled SERCA2a and 2CS stably expressed in HEK cells have $Ca^{2+}$-dependent ATPase specific activity comparable to pig cardiac SR, which expresses SERCA2a at a high level (20-30% of total protein).

GFP-RFP FRET in FLT Plate Reader.

The advent of the FLT-PR allowed us to rapidly obtain precise fluorescence waveforms from 96- or 384-well plates in under two minutes per plate (FIG. 2A). We previously showed that this plate reader could measure lifetimes from purified proteins in the same amount of time that a conventional plate reader measures intensity, but with a much better coefficient of variation (CV). (Cornea et al., *J Biomol Screen*, 2013, 18, 97-107). This was true to an even greater extent for cells stably expressing GFP-SERCA2a or 2CS (FIG. 2B). The 30-fold improvement in precision means that a very small change in lifetime can be detected reliably, creating an excellent high-throughput screen (FIG. 2C). We were initially concerned about optical interference from concentrated cell suspensions (up to ~2.5×10⁶ cells/mL), but found that both GFP-SERCA and 2CS stable cell lines were >30 times more fluorescent in the plate reader than untransfected cells at the same concentration. In contrast, our conventional intensity-mode fluorescence plate reader barely distinguishes GFP fluorescence from the background (CV~1). Cell density was optimized to minimize CV, and we found that a wide range of densities gave the same lifetime with high precision for both donor and donor-acceptor cells. $1\times10^6$ cells/mL gave CV values of 0.2-0.4% consistently for the GFP lifetime in both cell lines and this concentration was used for further experiments, however, we were able to obtain CVs as low as 0.34% with $<5\times10^4$ cells/mL (data not shown). This level of precision enables reliable detection of changes in lifetime on the order of 10 picoseconds (FIG. 2C). The donor-only lifetime on separate days was consistently 2.5±0.1 ns and the 2CS lifetime was 2.2±0.1 ns, giving a basal FRET efficiency of 0.12±0.05.

Figure 3:
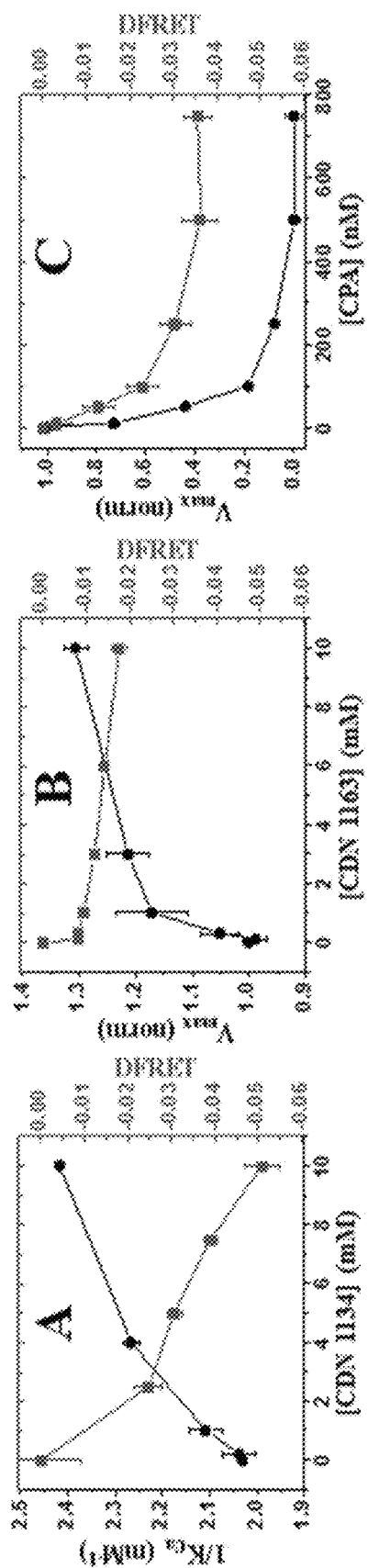

We previously carried out a screen based on FRET, (measured by fluorescence intensity), from dye-labeled SERCA to dye-labeled PLB in reconstituted membranes, resulting in several SERCA activators. (Cornea et al., *J Biomol Screen*, 2013, 18, 97-107). CDN1134 and CDN1163 represent two distinct classes of SERCA activators, with CDN1134 increasing the apparent $Ca^{2+}$ affinity of SERCA ($1/K_{Ca}$), and CDN1163 increasing the activity at saturating $[Ca^{2+}]$ ($V_{max}$). We found that these SERCA activators both reduce FRET between GFP and RFP in 2CS, with a dose dependence similar to that of SERCA activation (FIG. 3A,B). FRET in 2CS was also reduced by the known SERCA inhibitor cyclopiazonic acid (CPA), with a concentration dependence similar to that of inhibition (FIG. 3C). The FRET and functional data both yielded apparent $K_d$ values of about 40 nM, consistent with previous reports of the IC50 for inhibition of SERCA by CPA. (Michelangeli et al., *Biochem Soc Trans* 2011, 39, 789-797).

LOPAC Library Screen.

Figure 4:
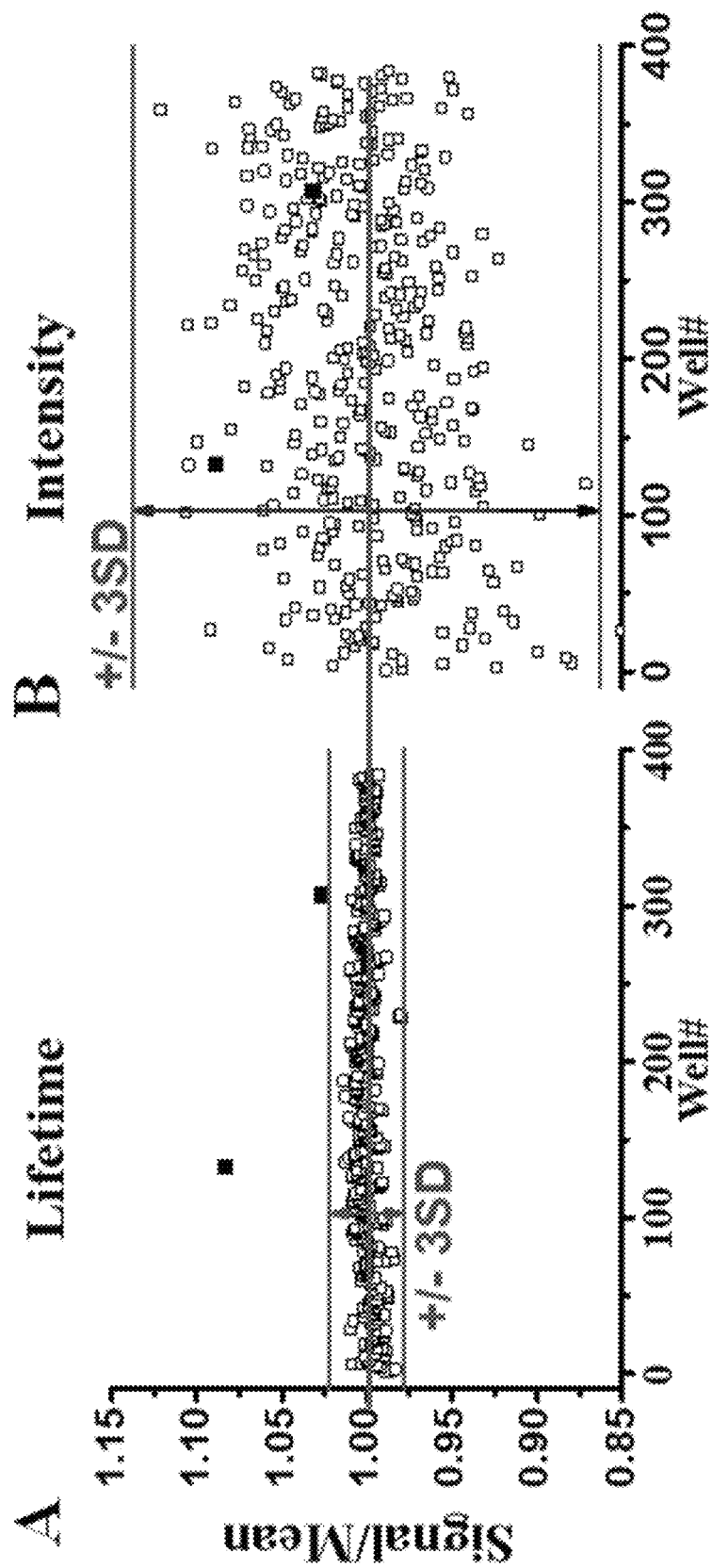
FIG. 4. Results from one of the four 384-well plates containing the 1280 compound LOPAC library. Lifetime fitting of waveforms (A) identifies two hits (solid symbols) that are SERCA effectors (TG and XCT 790), both of which are missed by intensity-based screening (B). Horizontal bars delimit the 3SD hit selection window.

The 1280-compound LOPAC library, arranged in 384-well plates, was scanned in the FLT plate reader. Compounds that caused the 2CS GFP lifetime to be outside the 3SD window from the mean (established in controls with DMSO only) were defined as hits. Assays on ten hit compounds were repeated to determine whether they were reproducible, and we found that seven of the hits were false positives. A 3SD cutoff predicts four random false positives for a screen of this size. We also eliminated compounds that caused fluorescence intensity to be more than 3SD outside the range of the 64 DMSO controls on each plate (7.1% of the library). FIG. 4 shows results from one of the LOPAC plates that contained two of the three reproducible hits. Both hits were clearly distinct from the other compounds and controls on the plate when the single-lifetime fits of the fluorescence decays were analyzed (FIG. 4A) In contrast, when analyzed by the conventional fluorescence intensity method, the hits were not distinguishable from the other compounds or controls (FIG. 4B). Intensity mode analysis has a much greater window to identify hits due to the much greater CV, and many false positives would be detected before either of the two true hits would be identified.

The three reproducible hits were thapsigargin (TG, Sigma Cat. No. T 9033), diphenyline iodonium chloride (DPI, Sigma Cat. No. D 2926), and XCT 790 (Sigma Cat. No. X 4752). TG is a well-known SERCA inhibitor that we did not know was present in the library, (Michelangeli et al., *Biochem Soc Trans* 2011, 39, 789-797) and DIC has also been shown to inhibit SERCA activity. (Tazzeo et al., *Br J Pharmacol* 2009, 158, 790-796). The third compound, XCT 790, is a well-known antagonist of the estrogen-like receptor α, (Ariazi et al., *Curr Top Med Chem* 2006, 6, 203-215). but has not been previously identified as an effector of SERCA activity.

Figure 5:
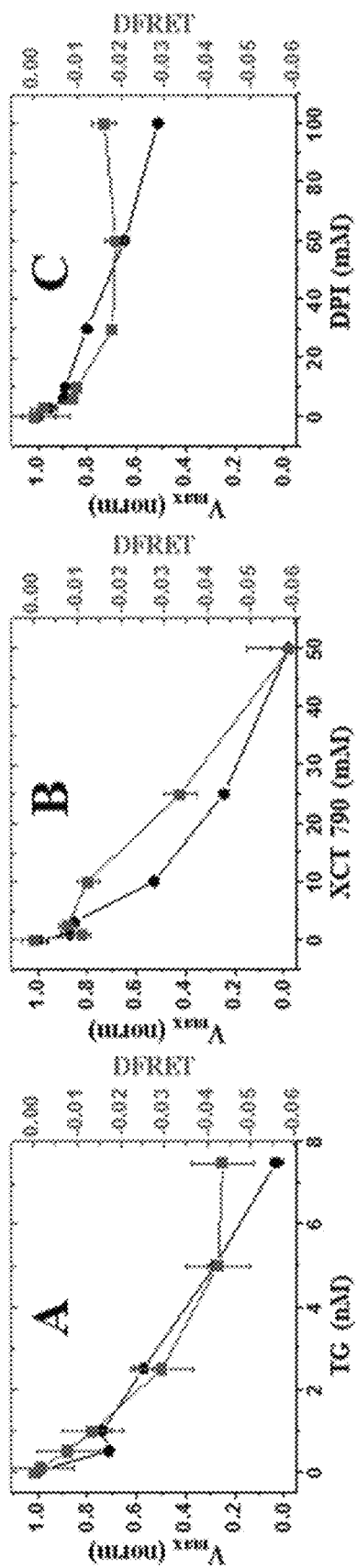
FIG. 5. FRET and functional effects of LOPAC compounds identified in the screen. All three compounds reduce FRET and inhibit ATPase activity in a dose-response manner with similar dose dependence. TG (A) and XCT 790 B) completely inhibit ATPase activity at the highest concentrations tested, while DPI inhibits <50% of ATPase activity at 100 mM (C).

TG was the most potent FRET effector in both the LOPAC screen and subsequent dose-response assays, reducing FRET by ~33% at only 7.5 nM, when ATPase activity is nearly ablated (FIG. 5A). This result is consistent with previous steady-state FRET results of 2CS, which showed TG promoting a more open, low-FRET headpiece conformation. (Hou et al., *PLoS ONE* 2012, 7, e40369).

XCT 790 was also a strong FRET effector, reducing FRET by ~42% while inhibiting ATPase activity with similar concentration dependence (FIG. 5B). XCT 790 is yellow in color when dissolved in DMSO, but it did not contribute any fluorescence intensity to plate reader measurements and had no effect on the lifetime of GFP-SERCA2a alone.

The third hit, DPI, was the weakest FRET effector, maximally reducing FRET from 0.12 to 0.10 (~18%). However, the FRET change was extremely reproducible and the concentration dependence of DPI was again similar to that of ATPase inhibition (FIG. 5C). The ATPase dependence is very similar to a previous report showing 18% inhibition of $Ca^{2+}$ uptake into microsomes with 30 μM DPI and 32% inhibition at 100 μM DPI. (Tazzeo et al., *Br J Pharmacol* 2009, 158, 790-796).

Discussion

SERCA activation is a sought-after therapeutic goal to treat a wide variety of diseases including HF, (Inesi et al., *Biochem Biophys Res Commun* 2008, 369, 182-187) muscular dystrophy, (Gehrig et al., *Nature* 2012, 484, 394-398; Goonasekera et al., *J Clin Invest* 2011, 121, 1044-1052) and diabetes, (Fu et al., *Nature* 2011, 473, 528-531) and SERCA inhibitors are sought for cancer therapeutics. (Hermanson et al., *Mol Pharmacol* 2009, 76, 667-678). Many approaches have been taken to achieve the desired aim of increasing SERCA activity and reducing cytosolic $[Ca^{2+}]$. In this respect, gene therapy to overexpress SERCA2a in the heart is quite effective as a means to enhance Ca-transport capacity. Phase II clinical trials showed improvement in hemodynamic parameters and quality of life when patients were treated with an adeno-associated viral vector expressing SERCA2a in the heart. (Jessup et al., *Circulation* 2011, 124, 304-313). These results show that normalizing $Ca^{2+}$ cycling in failing hearts mitigates disease symptoms and improves muscle function. However, only about 50% of the HF patients qualify for the gene therapy approach, due to the prevalence of AAV neutralizing antibodies in the general population. Small-molecule SERCA activators are designed to restore $Ca^{2+}$ cycling by activating existing SERCA pumps in the SR, and are expected to provide a more mainstream pharmacological therapy for HF patients without the limitations currently associated with gene therapy.

We previously conducted a FRET-based high-throughput screen to detect small molecules that disrupt the interaction between SERCA and PLB. (Cornea et al., *J Biomol Screen*, 2013, 18, 97-107). Several compounds were identified in that screen as SERCA activators, but none were specific for the SERCA-PLB interaction. Those compounds were apparently allosteric SERCA activators that directly perturbed the structure of SERCA and altered SERCA-PLB FRET as a result. Here, by placing both donor and acceptor probes within SERCA, we have searched exclusively for compounds that directly affect SERCA.

Crystal structures of SERCA1a show large rearrangements of the cytoplasmic headpiece during the enzymatic cycle, with large (~3 nm) changes in distance between the N and A domain, making them ideal locations for FRET probes to find functional effectors. Previous studies showed that a CFP-SERCA fusion protein actively pumps $Ca^{2+}$ and is properly localized to intracellular membranes, and that FRET is sensitive to both TG inhibition and $Ca^{2+}$ activation. (Hou et al., *PLoS ONE* 2012, 7, e40369). Here we have confirmed the result that TG promotes a more open SERCA headpiece and that stably expressed 2CS in HEK cells is sensitive to allosteric regulators, thus suitable to use in screens for small molecules that perturb SERCA structure.

Using the fluorescence lifetime plate reader, we have developed the first high-throughput fluorescence lifetime assay in living cells. The precision of the lifetime measurement (CV=0.3%) allowed us to detect very small changes in FRET between GFP and RFP, and we showed that this FRET signal is sensitive to both activators and inhibitors of SERCA function. Compounds tested showed similar concentration dependence for FRET and ATPase assays, indicating a tight link between structural and functional perturbations.

Our pilot-scale screen of the LOPAC library did not uncover any new activators, but we did identify two known inhibitors and a new inhibitor, XCT 790. Each of these hits showed similar FRET and ATPase concentration dependence, supporting a strong connection between the measured structural perturbations and enzyme function. DPI is also interesting because it was identified in a 2006 screen of the LOPAC library as a compound that inhibited growth of the malarial parasite *Plasmodium falciparum*. (Yuan et al., *Nat Chem Biol* 2009, 5, 765-771). The SERCA-like pump in this parasite is a target for the development of new drugs to treat drug-resistant strains of malaria. (Arnou et al., *Biochem Soc Trans* 2011, 39, 823-831). The $IC_{50}$ for inhibition of parasite growth was submicromolar, while both the ATPase data here and $Ca^{2+}$ uptake assays reported previously agree that there is very little functional inhibition below 10 µM. (Tazzeo et al., *Br J Pharmacol* 2009, 158, 790-796). While DPI may prove to be an effective treatment for drug resistant malaria, the connection between SERCA inhibition, structural perturbation, and restriction of *P. falciparum* growth remains unclear.

Structures obtained from crystals grown in the presence of TG have shown a compact (closed) headpiece conformation, (Inesi et al., *Biochemistry* 2006, 45, 13769-13778) but our results with 2CS suggest that TG opens the headpiece in living cells (FIG. 5A), consistent with previous results. (Hou et al., *PLoS ONE* 2012, 7, e40369).

The assay presented here shows promise for large-scale FLT-based HTS campaigns using living cells, including, but not limited to, identifying new SERCA activators or inhibitors. The FLT-PR enables detection of very small changes with high precision, and here we show that the instrument is capable of measuring lifetimes precisely in live cells. Two-color constructs could be made with other SERCA isoforms or different proteins that undergo conformational changes associated with function. Increased activity (through overexpression) of the SERCA1a isoform in skeletal muscle has shown promise in treating muscular dystrophy, (Goonasekera et al., *J Clin Invest* 2011, 121, 1044-1052; Morine et al., *Hum Gene Ther* 2010, 21, 1735-1739) and overexpression of SERCA2b in non-muscle cells slows the progression of diabetes in mouse models. (Park et al., *Proc Natl Acad Sci USA* 2010, 107, 19320-19325). Thus the identification of new SERCA activators, whether they are isoform-specific or not, could generate new drugs that treat several of the most common and costly diseases.

Example 2

Fluorescence Lifetime Plate Reader: Resolution and Precision Meet High-Throughput Described here is a nanosecond time-resolved fluorescence spectrometer that acquires fluorescence decay waveforms from each well of a 384-well microplate in 3 min with signal-to-noise exceeding 400 using direct waveform recording. The instrument combines high-energy pulsed laser sources (5-10 kHz repetition rate) with a photomultiplier and high-speed digitizer (1 GHz) to record a fluorescence decay waveform after each pulse. Waveforms acquired from rhodamine or 5-((2-aminoethyl)amino) naphthalene-1-sulfonic acid dyes in a 384-well plate gave lifetime measurements 5- to 25-fold more precise than the simultaneous intensity measurements. Lifetimes as short as 0.04 ns were acquired by interleaving with an effective sample rate of 5 GHz. Lifetime measurements resolved mixtures of single-exponential dyes with better than 1% accuracy. The fluorescence lifetime plate reader enables multiple-well fluorescence lifetime measurements with an acquisition time of 0.5 s per well, suitable for high-throughput fluorescence lifetime screening applications.

Materials and Methods

A. Instrument

Figure 6:
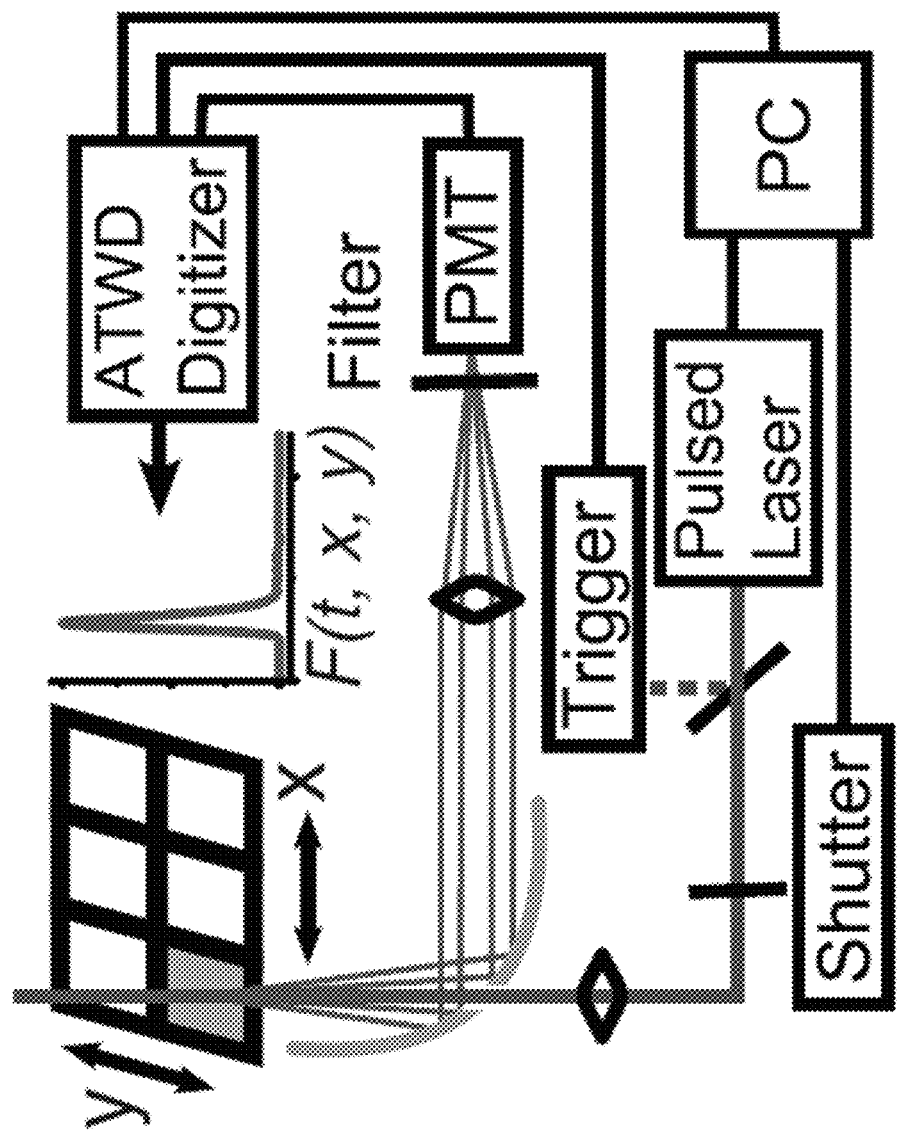
FIG. 6. Fluorescence lifetime plate reader. The NovaFluor spectrometer uses an X-Y stage, pulsed laser, PMT, and digitizer for direct waveform recording (DWR) of fluorescence lifetime decays. Excitation light is focused through a pinhole to the center of each well of a microplate. Fluorescence emission is collimated by a parabolic mirror and focused on the PMT. Fluorescence decays are digitized and acquired for lifetime or moment analysis.

The NovaFluor plate reader (FIG. 6) was designed and built by Fluorescence Innovations, Inc. We performed 355 and 532 nm excitation with a 10 kHz pulse rate using an yttrium-aluminum-garnet microchip laser (JDS Uniphase) followed by a frequency multiplier and bandpass filter. We excited at 473 nm with a 5 kHz pulse rate using an FP2-473-3-5 microchip laser with LD-702 controller (Concepts Research Corporation). Excitation light passed through a neutral density filter and then through a pinhole in a collector mirror fixed beneath the moving stage. Fluorescence was gathered by the parabolic mirror for detection. Emission filters (470/20 nm band pass or 590/10 nm band pass) were placed before the detector, a H10270-20 photomultiplier tube (Hamamatsu) operating at 400 V except as noted. Detector current was converted to voltage at 50 by a custom circuit board based on a 1 GHz analog transient waveform digitizer (ATWD version 3.1). (Kleinfelder, Proc. SPIE, 4858, 316 (2003)). Motors driving the X-Y stage, shutter, neutral density, and emission filters were controlled by a second custom board. All controllers were routed to USB using an RS-232 serial adapter. Instrument control and data acquisition were performed with custom software on a personal computer. We used an Ophir PD-10v2 power meter to calibrate neutral density filter position.

B. Fluorescent Dyes

Solid dyes were dissolved to ~1 mM in spectroscopic grade ethanol and stored at −20° C., except EDANS (5-((2-aminoethyl)amino) naphthalene-1-sulfonic acid) which was dissolved in N,N-dimethyl-formamide. Working solutions were diluted to 1 µM (except as noted) in de-ionized water. Rhodamine B and 6G were excited at 473 nm, EDANS at 355 nm, and Rose Bengal at 532 nm. Fluorescence decays were acquired (FIG. 7) using a neutral density filter to adjust the peak signal to near 100 mV with 50-150 mV as an optimal range (1-3 mA peak output current of the PMT). We recorded decay waveforms with 640 samples at 0.2 ns resolution (128 ns total time). The signal delay was adjusted to allow at least 40 samples (8 ns) of pre-excitation data used to adjust the signal baseline.

C. Microplate Preparation

We loaded plates manually with a multichannel pipet (ThermoFisher) or automatically with a FlexDrop IV dispenser (PerkinElmer). We used well volumes of 50 or 100 µl a 384-well glass-bottomed Greiner SensoPlate. Dye mixtures were dispensed in volumes with 5 µl increments. Plates were spun briefly (up to 300 rpm in Eppendorf rotor 5810R voltage, and other factors and was acquired daily from a single well of de-ionized water with neutral density filter adjusted to a 100 mV peak signal.

D. Data Analysis

Analysis of total fluorescence and first moment was performed in Microsoft Excel or (Matlab (MathWorks). Total fluorescence was calculated as $\Sigma_i F(t_i)$, where F(t) was the signal intensity after baseline correction. Lifetime analysis used custom software to simulate exponential decays convolved with the measured IRF for fitting using nonlinear least squares (Levenberg-Marquardt algorithm.) For single dyes, a lifetime model was used:

$$F(t) = A \exp\left(-\frac{t-\Delta}{\tau}\right), \quad (1)$$

where A was the amplitude of fluorescence, $\tau$ was fluorescence lifetime, and $\Delta$ was a parameter accounting for time shift between the signal and the IRF.

Mixtures were averaged across replicate wells and fit to $$F_j(t) = C_j[x_j A_1 \exp[-(t-\Delta)/\tau_1] + (1-x_j) A_2 \exp[-(t-\Delta)/\tau_2]] \quad (2)$$

where $x_j$ was the mole fraction in the jth mixture and $C_j$ was a scaling factor to account for intensity-dependent noise. Lifetimes $\tau_1, \tau_2$ were globally constrained (Beechem et al., Numer. Comput. Methods, 210, 37 (1992)) to the values obtained for pure dye. Time shift $\Delta$ and amplitudes $A_1, A_2$ were globally fit. Amplitude terms reflected the combined effect of extinction coefficient and quantum yield in the two dyes and fraction x represented the ratio of dye molecules. We found constraining the start (x=0) and end fractions (x=1) using single dyes improved fit accuracy.

(Raw first moments were defined as $\Sigma F(t_i)/F(t_i)$ and adjusted using exponential depression (Gakamsky et al., Anal. Biochem., 409, 89 (2011); Thorne et al., Curr. Opin. Chem. Biol., 14, 315 (2010)) to suppress noise at longer time intervals. We used the raw first moment $\mu^0$ to calculate a depression function, $\exp(-t/\beta\mu^0)$. Larger $\beta$ values increased agreement of the moment and lifetime values, but decreased precision. We found $\beta=3$ was sufficiently small to maintain precision. The adjusted first moment, $$\mu = \frac{1+\beta}{\beta}\left[\frac{\sum_i t_i \exp(-t_i/\beta\mu^0) F(t_i)}{\sum_i \exp(-t_i/\beta\mu^0) F(t_i)}\right], \quad (3)$$

was calculated by assuming that F(t) was an exponential function (Eq. (1)). Integration of Eq. (3) by parts would then yield $\mu=\tau$ in an ideal case where the IRF is infinitely steep.

III. Experimental Results

The NovaFluor plate reader is a nanosecond time resolved spectrometer that uses pulsed laser excitation, a high-speed digitizer, and a photomultiplier tube (PMT) detector to record fluorescence decays from each well of a microplate. The digitizer read time is approximately 1 ms per waveform for a 5 kHz laser source (interleaving over 5 pulses) and the transport time is 0.3 s per well. Typical acquisitions were averaged across 200 successive waveforms giving an acquisition rate of 0.5 s per well or 3 min per 384-well plate. We used single-lifetime dyes to determine the precision and resolution of the plate reader and to measure its signal-to-noise performance.

A. Lifetime Compared with Intensity

Figure 8:
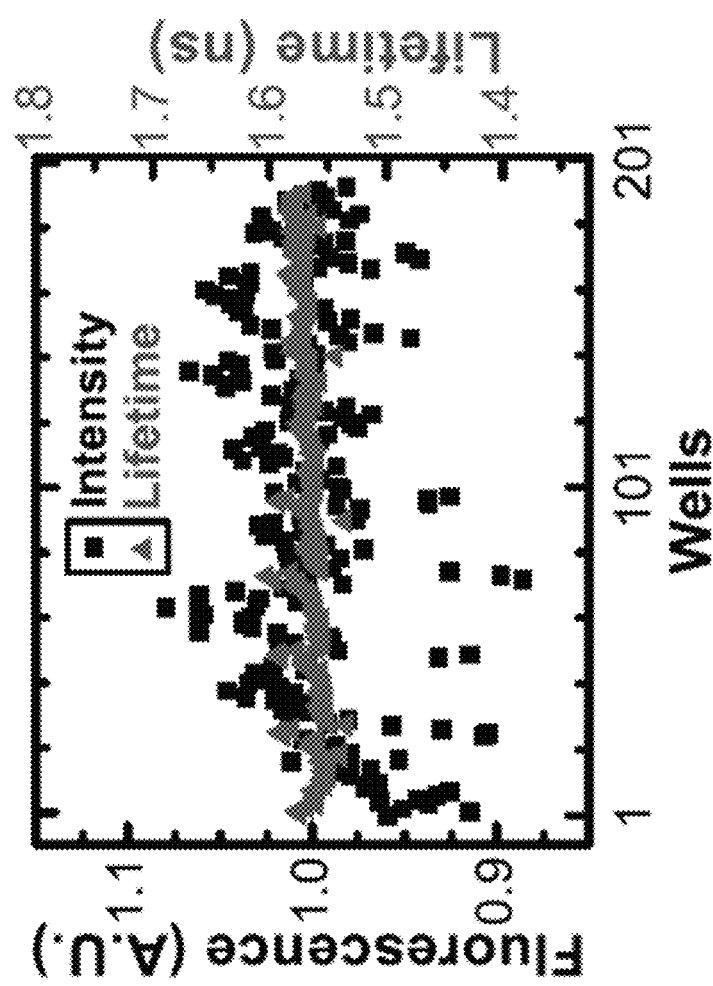
FIG. 8. Fluorescence lifetime is more precise than fluorescence intensity. Intensity (squares) and lifetime (triangles) of rhodamine B (1 µM in water) were calculated from waveforms acquired in 192 wells of a 384-well microplate. Lifetime CV is 0.7% (coefficient of variation=SD/mean), 5-fold more precise than intensity CV (3.5%) for this short lifetime dye. Left axis is total intensity divided by mean and right axis is centered and scaled in proportion.

We used water-soluble dyes with a variety of lifetimes to measure instrument performance (FIG. 8). First we measured the instrument response function (IRF) in pure water. We then selected an appropriate emission filter and adjusted excitation power with a neutral density filter to give a peak signal of 50-150 mV. Total intensity was measured as the fluorescence decay integrated across all time points of the acquired waveform. Lifetime and moment were determined from the waveform (see Sec. II of this example).

The plate reader acquired lifetime data with better than 1% precision for dye lifetimes of 1.6 ns and higher. Precision was measured as coefficient of variation (CV=SD/mean). Lifetime measurements were up to 25-fold more precise relative to the simultaneous measurement of total intensity. The ultra-short lifetime dye Rose Bengal fit to a single lifetime (0.04 ns) with low precision, although the standard deviation (11 ps) was comparable to that of other dyes.

We measured the precision of lifetime detection by uniformly dispensing dye into 384-well plates and measuring the DWR signal using the plate reader (FIG. 8). We fit the decays to a single exponential lifetime model (Eq. (1)). We found rhodamine B lifetime had 5-fold improved precision compared with total intensity, while the longer lifetime dyes rhodamine 6G and EDANS showed a 25-fold relative improvement in precision (Table I). We would expect DWR to have better precision for lifetimes that are long relative to the IRF (2.8 ns FWHM), and this is consistent with our results. In most cases we found that well-to-well precision improved when analyzing half of each plate (192 wells) due to systematic errors in volume of liquid dispensed.

TABLE I

Comparison of precision for intensity, lifetime, and moment measurements. Dyes were dispensed in uniform volume in microplates to measure signal precision across wells. Lifetime precision (coefficient of variation, CV = SD/mean) is superior to intensity precision in all but the shortest lifetime dye. Further enhancement of precision is seen in the adjusted first moment.

|  | Intensity CV | Lifetime (ns) | Lifetime SD (ns) | Lifetime CV | Moment (ns) | Moment SD (ns) | Moment CV |
|---|---|---|---|---|---|---|---|
| Rose Bengal | 7.17% | 0.040 | 0.011 | 27.50% | 1.187 | 0.004 | 0.34% |
| Rhodamine B | 3.47% | 1.566 | 0.010 | 0.67% | 2.476 | 0.009 | 0.37% |
| Rhodamine 6G | 6.99% | 3.914 | 0.011 | 0.27% | 3.357 | 0.008 | 0.25% |
| EDANS | 2.74% | 12.684 | 0.028 | 0.11% | 10.197 | 0.014 | 0.14% |

We also analyzed waveforms using first moment, a more direct analysis than the lifetime model. We found the raw first moment had poor precision and was sensitive to noise during the later fluorescence decay, even when we truncated the data. The adjusted first moment (Eq. (3)) had greater precision than was seen in the fitted lifetimes. The absolute value of the moment differed from the value of lifetime and was affected by experimental conditions such as PMT voltage.

Figure 9:
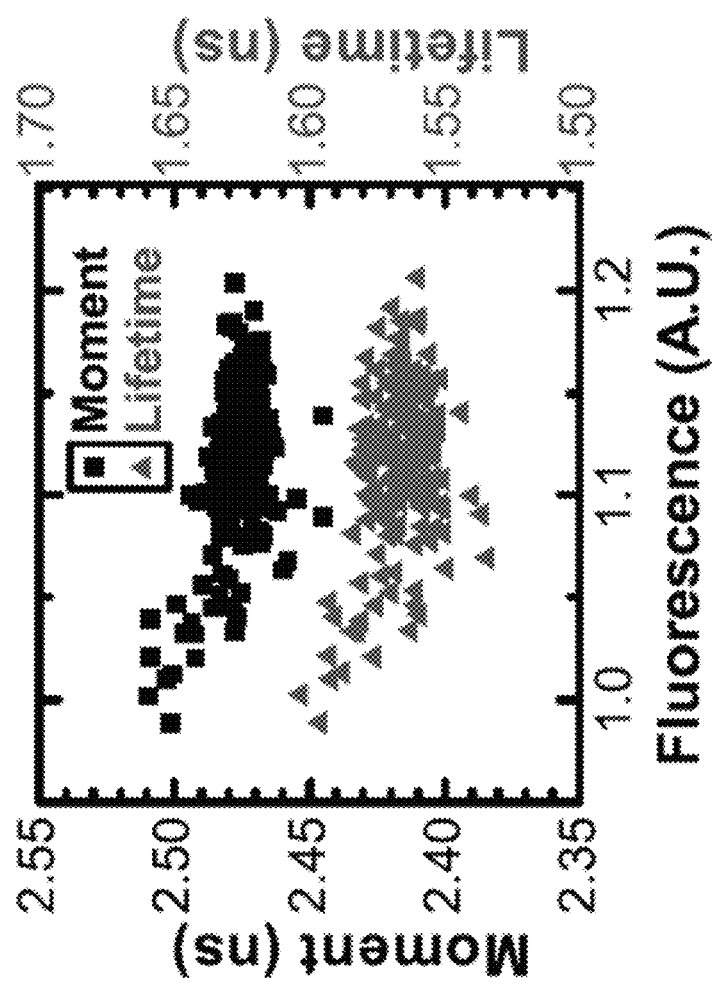
FIG. 9. Lifetime and moment are precise across wells. Lifetime and adjusted moment of rhodamine B (1 µM in water) were calculated from the decay waveform in each well. CV was 0.67% (SD 10 ps) for lifetime and 0.22% (SD 9 ps) for moment. CV (coefficient of variation)=SD/mean. One fluorescence unit=total intensity given a peak signal of 100 mV.

We examined variation between wells by comparing total intensity with lifetime and adjusted first moment (FIG. 9). Lifetime values for the dyes in Table I were mostly randomly distributed, showing weak correlation with intensity (Pearson's correlation coefficient r took values |r|≤0.5). Rhodamine 6G showed a moderately strong correlation (r=0.87) with intensity, although the coefficient of variation remained less than 1%. We hypothesize that these correlations reflect a small nonlinear response in the detector and/or digitizer.

B. Linearity of Detection

Figure 10:
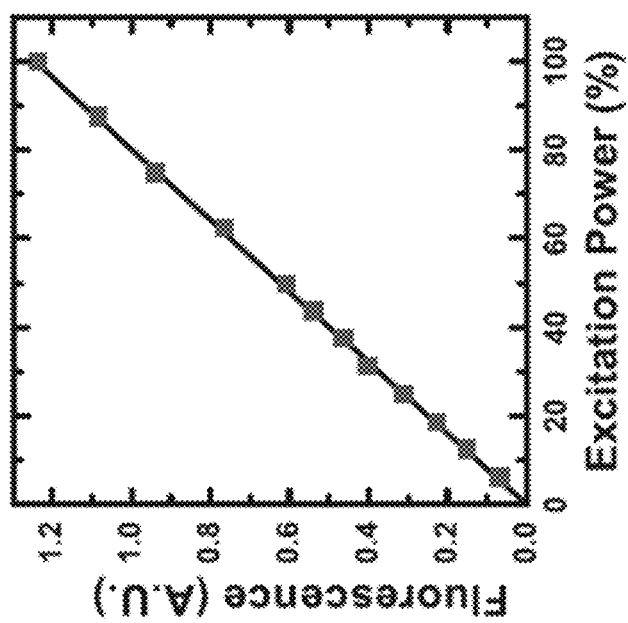
FIG. 10. Linear dependence of fluorescence on excitation power. Incident power was varied by a neutral density filter to excite Rose Bengal (1 µM in water) in a single well. Total intensity (squares) varied linearly ($r^2 > 0.999$; RMSD 0.90%). Black line is the predicted relationship, scaled to the unit intensity of a waveform at 100 mV peak signal.

Direct waveform recording requires fluorescence emission to be linearly related to signal intensity, since intensity dependent variations could distort the waveform and fitted lifetime. (Muretta et al., Rev. Sci. Instrum., 81, 103101 (2010)). We varied excitation power and sample concentration to determine whether nonlinearity affected instrument performance. First, we tested linearity of the total intensity measurement by reducing the excitation power in calibrated steps and measuring intensity of the ultra-short lifetime dye Rose Bengal, finding excellent agreement (FIG. 10). We defined an arbitrary unit of fluorescence as the total intensity of a given waveform with a 100 mV peak signal.

Figure 11:
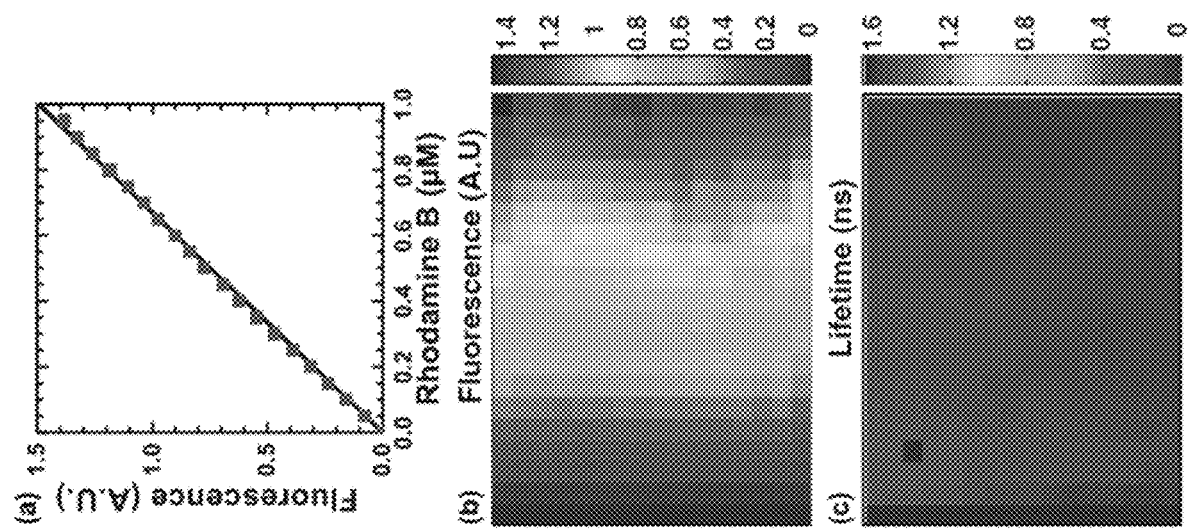
FIG. 11. Fluorescence is proportional to intensity. (a) Fluorescence total intensity (squares) of rhodamine B (0-950 µM in water) varies linearly with concentration (r2>0.999; RMSD 1.8% relative to expected relationship shown in black line). (b) Intensity map of plate shown in false color with dye concentration ranging from 0 (left column) to 950 µM (right column). (c) Lifetime map of the same plate, with wells empty of rhodamine assigned a lifetime of zero.

Next we tested how fluorescence intensity varied with concentration of the short lifetime dye rhodamine B over a 50-950 nM range (FIG. 11(a)) and found the expected linear relationship with a root-mean-squared deviation of 1.8%. For this experiment, each dye concentration was dispensed in 16 replicate wells. CV of intensity was 2%-6% in each set of replicates and CV of lifetime was 1.64% across all wells, varying from 2.08% at 50 nM to 0.87% at 950 nM.

Figure 12:
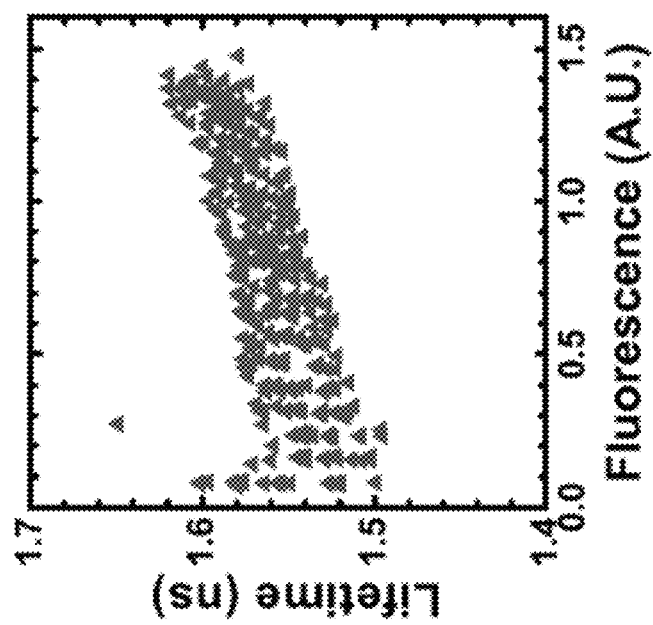
FIG. 12. Distribution of apparent fluorescence lifetime and intensity. Fitted lifetimes (triangles) were precise (1.6% CV) across a range dye concentrations (50-950 µM rhodamine B in water). The apparent correlation of lifetime and intensity reflects detector nonlinearity. CV=coefficient of variation (SD/mean).

We further analyzed the effect of signal intensity on apparent lifetime by plotting lifetime and intensity for each well (FIG. 12). Lifetime values were increasingly variable below 0.5 A.U., while the instrument provided good precision for fluorescence signals in the range 0.5-1.5 A.U. The apparent lifetime showed a moderate positive correlation with intensity (r=0.70) despite the overall low CV (1.6%). This correlation had minimal impact on precision when intensity variation was due to experimental error alone. For example, the data in (FIG. 9) span a range of ~1.0-1.2 A.U. with a lifetime CV of 0.7%. The lifetime of rhodamine B (1.6 ns) was short compared to the IRF (2.8 ns) and thus was more affected by instrument nonlinearity than were the longer lifetime dyes.

C. Signal Quality

Figure 7:
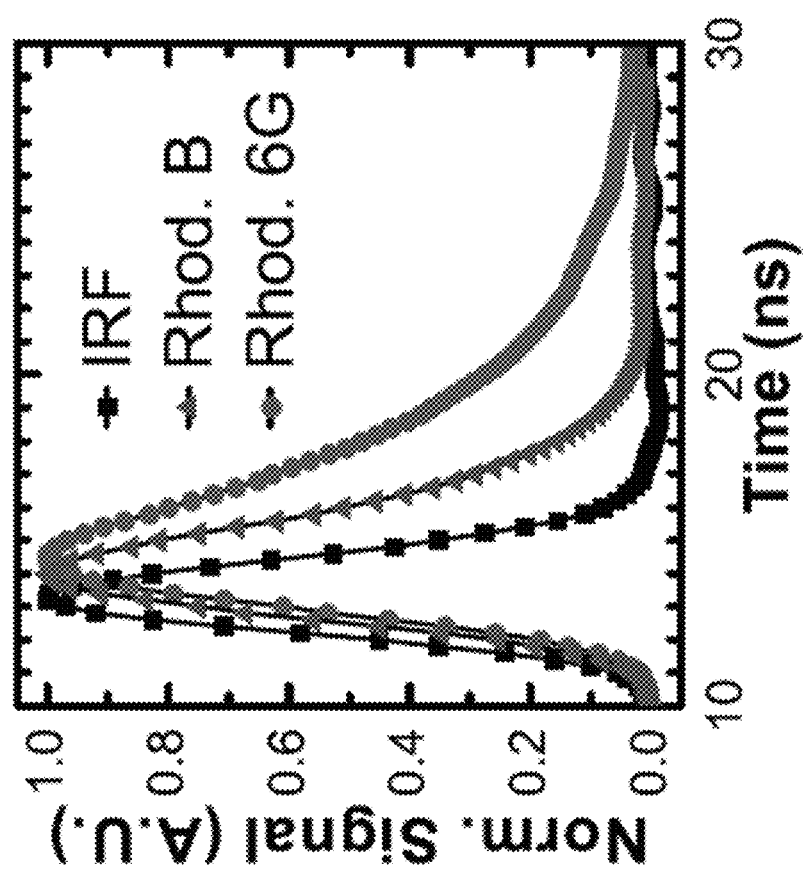
FIG. 7. Direct Waveform Recording (DWR) of Fluorescence Decays. The instrument response function (IRF, squares) acquired from scattering in water is shown with fluorescence decay waveforms for rhodamine B (triangles) and rhodamine 6G (circles). Waveforms acquired by DWR at 400 V with 0.2 ns resolution. Signal does not start at time zero because pre-excitation data were used to adjust the Y-axis baseline for each normalized waveform.
Figure 13:
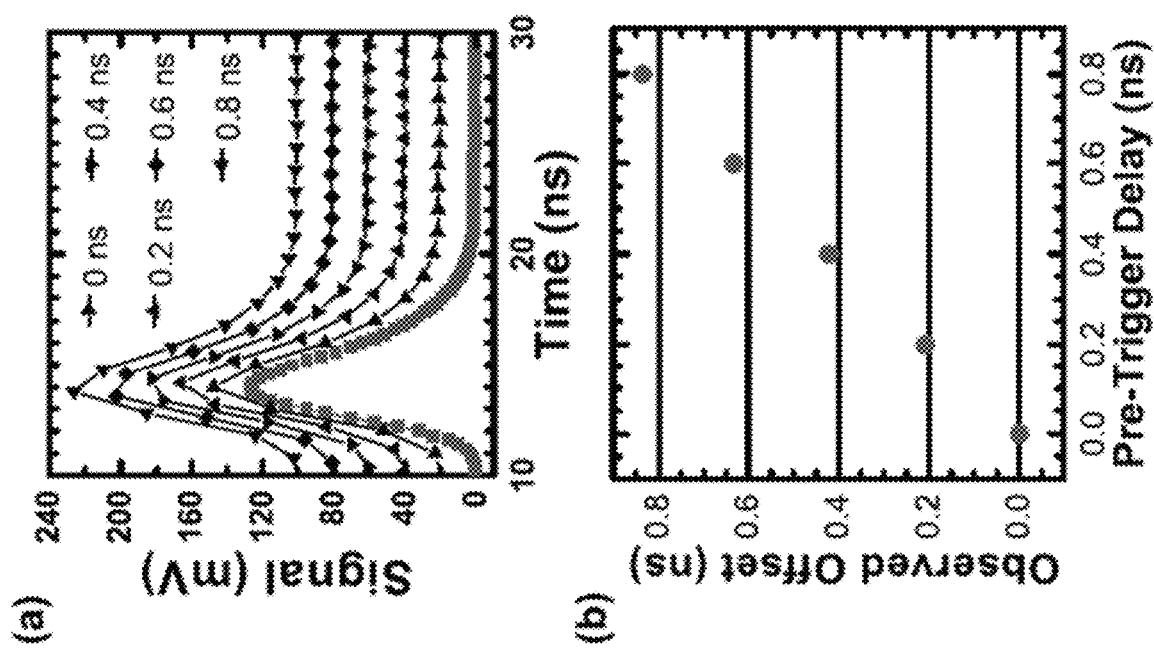
FIG. 13. Pulse interleaving increases effective sampling rate. (a) The ATWD digitizer was calibrated to use a series of pre-trigger delays (symbols: 0, 0.2, 0.4, 0.6, and 0.8 ns) on successive laser pulses. Each sequence of five 1-GHz acquisitions was combined into a single 5-GHz interleaved waveform (squares). (b) The true offsets (circles) were measured by exponential fitting showing better than 5% agreement with calibrated values (X-axis), root-mean-squared deviation 2.8%.

The instrument response function (IRF) had a measured FWHM of 2.3 ns (full width at half maximum) with 355 nm excitation and 2.8 ns with 473 nm excitation (FIG. 7). In all experiments we acquired waveforms at 1 GHz with the ATWD digitizer and increased the effective sample rate to 5 GHz by interleaving each cycle of 5 laser pulses (FIG. 13(a)). We calibrated a series of onboard pre-trigger delays in 0.2 ns steps so that the delay incremented with each laser pulse. We verified the delay calibration by recording 200 successive 5 GHz waveforms of a rhodamine B sample and extracting the 1 GHz waveforms. We then fit the time delay relative to the IRF for each waveform and calculated mean offset values (FIG. 13(b)). The observed offsets had better than 5% accuracy over 6 months compared with calibrated values.

Figure 14:
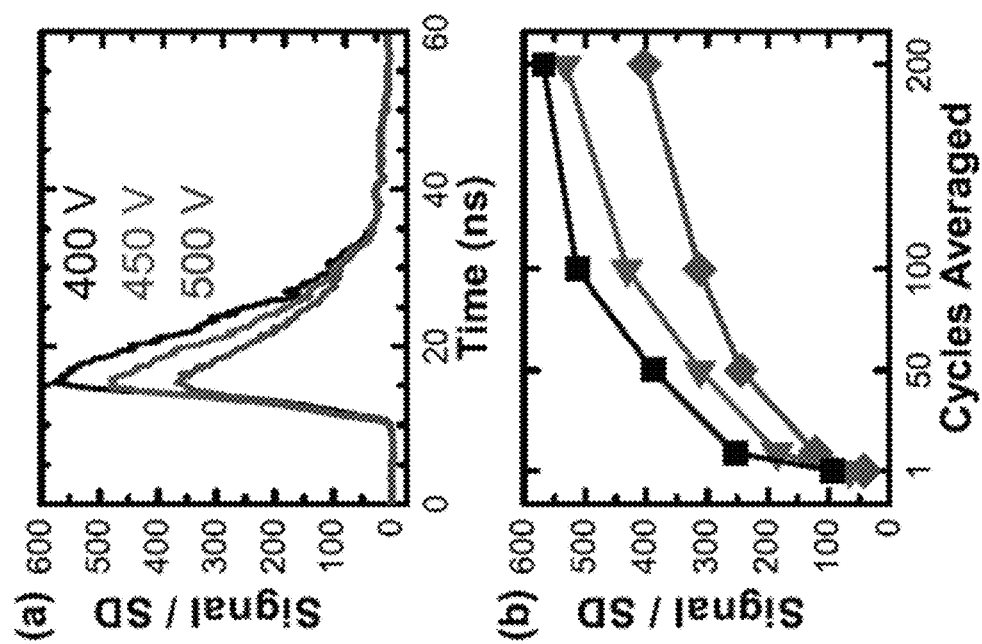
FIG. 14. Direct waveform recording provides high SNR. Signal-to-noise ratio (SNR, defined as signal/SD) was measured for 1000 successive acquisitions with 0.2 ns resolution. (a) SNR waveform of rhodamine 6G (1 μM in water) acquired with 200 cycle averaging of each waveform; (b) Representative values of peak SNR of rhodamine 6G with varied number of cycles averaged. Peak SNR was highest (580) at low PMT voltage (400 V, squares) and dropped to 360 at high PMT voltage (500 V, diamonds).

The ability to precisely acquire lifetime data depends on the experimental signal-to-noise ratio (SNR), typically measured at the peak of the fluorescence decay. (Moger et al. Screening, 11, 765 (2006); Muretta et al., Rev. Sci. Instrum., 81, 103101 (2010)). We acquired 1000 signal-averaged waveforms from a sample of rhodamine 6G in order to estimate instrument noise from the variation in a single well. We calculated the SNR waveform (FIG. 14(a)) as the signal of one waveform divided by the standard deviation at each time point. Peak SNR was inversely related to the detector voltage. At the low PMT voltage (400 V, a detector gain of about 1000) SNR peaked at 580 and dropped to 360 at higher PMT voltage (500 V, a detector gain of about 5000). These values were far above the desired threshold for precise lifetime detection (SNR≥100).

The maximum signal-to-noise ratio was affected by the PMT voltage and the number of cycles averaged (FIG. 14(b)). In the absence of averaging, SNR ranged from 40 at 400 V acquisition to 90 at 500 V. Averaging over 200 cycles per acquisition increased SNR better than 6-fold. Experimental sources of variation between wells had a large effect on lifetime precision relative to instrumental sources. We found a 384-well plate of rhodamine 6G that showed substantial well-to-well variation in observed lifetime (CV 1.62%) with 200 cycles of averaging showed nearly equal precision with 50 cycles of averaging (CV 1.64%) despite the nearly 50% decrease in SNR per well. Pulse interleaving had a modest effect in the presence of experimental noise. Interleaved waveforms (5 GHz) of the short lifetime dye rhodamine B were more precise across wells (CV 0.59%) than the same waveforms without interleaving (1 GHz, CV 0.87%).

D. Resolution of Lifetimes

Figure 15:
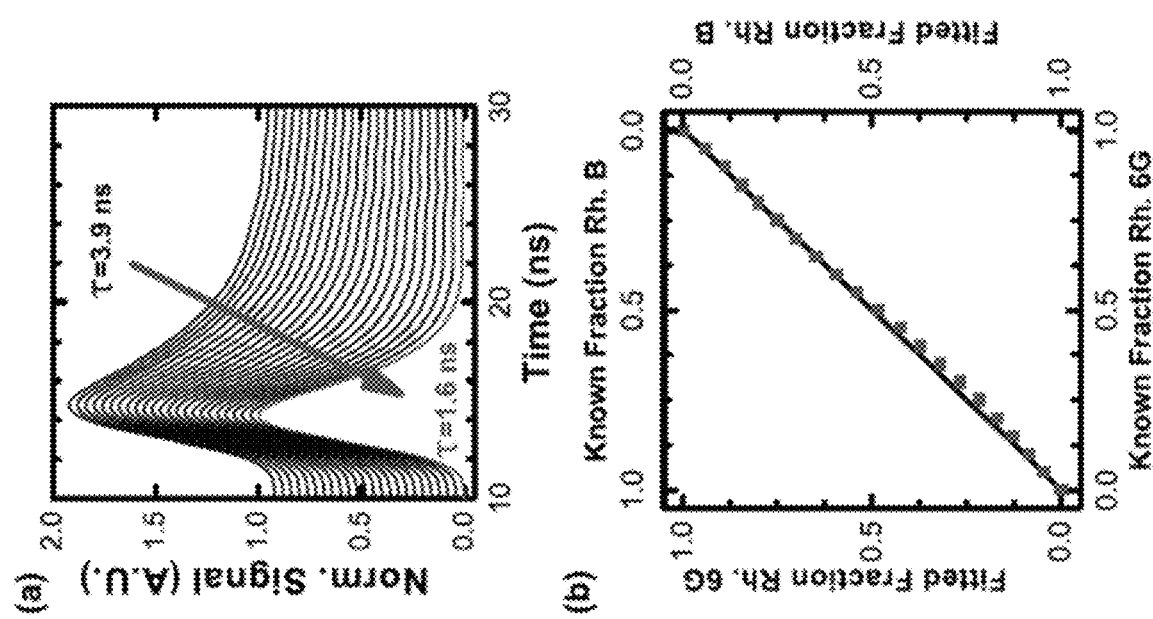
FIG. 15. Fluorescence lifetime quantitatively resolves dye mixtures. (a) Rhodamine 6G was mixed with rhodamine B in 5% volume steps (1 μM total, in water) for lifetime detection. (b) The mole fraction of rhodamine 6G was recovered with high accuracy by a two-component exponential fit (squares). Squared correlation coefficient $r^2 > 0.999$, root-mean-squared deviation 0.74% relative to the predicted relationship x=y (black line).

We tested the ability of the plate reader to resolve two dyes with similar lifetimes (1.6 ns for rhodamine B and 3.9 ns for rhodamine 6G) and overlapping emission spectra by mixing the dyes in 384-well plate, incrementing the volume of each dye by 5% in each column of wells to maintain a total concentration of 1 μM (FIG. 15). We averaged 16 replicate wells at each concentration and fit the relative fraction of dye using a two-component model (Eq. (2)). The fit recovered the true fraction with high accuracy (root-mean-squared deviation (RMSD)=0.74% relative to the predicted mole fractions). The two-component mixture required averaging of replicate wells as fit results showed high variability (RMSD 2% or greater). Variability decreased to 1.08% RMSD with 4 replicates and 0.74% with 16. This result demonstrates the NovaFluor plate reader is capable of resolving changes in lifetime with high accuracy, a key requirement for lifetime-based assays.

IV. Discussion

Direct waveform recording (DWR) enables fluorescence lifetime acquisition in a microplate with a signal-to-noise ratio (SNR) of 400 or better while maintaining acquisition rates of 0.5 s per well. The plate reader acquires waveforms with high precision across a range of lifetimes, from short (1.6 ns, rhodamine B) to long (12.7 ns, EDANS). While there is great interest in developing long lifetime probes to improve the resolution of lifetime assays, (Maltman et al., Chem. Commun., 46, 6929 (2010)) the high precision of DWR permits the use of short lifetime probes as well. The per-well precision of lifetime measurement is routinely near 10 ps allowing us to resolve small changes in lifetime with high precision. The width of the IRF (2.8 ns) was not a barrier to analysis of short lifetimes, although the ultra-short lifetime dye Rose Bengal was unsuitable.

Fluorescence lifetime has a key advantage in high-throughput screening assays because it directly resolves interfering fluorescence signals (Acker et al., Perspect. Sci., 1, 56 (2014)) that are present in most screening compound libraries. (Simeonov et al., J. Med. Chem., 51, 2363 (2008)). The use of multiple-exponential fits to resolve compound interference is firmly established. (Gakamsky et al., Anal. Biochem., 409, 89 (2011)). We have shown (FIG. 15) that the DWR plate reader resolves the relative fraction present in a two-component mixture with better than 1% accuracy over a 20-fold concentration range, making it resistant to compound interference.

Acquisition rate has been a key limitation in applying fluorescence lifetime to high-throughput screening. We can compare DWR with photon counting methods of lifetime detection by comparing peak SNR in each. In photon counting, (Moger et al. Screening, 11, 765 (2006)) SNR increases as $\sqrt{N}$, while DWR measures SNR as signal/SD of successive waveforms. (Muretta et al., Rev. Sci. Instrum., 81, 103101 (2010)). Photon counting applications have been optimized for a CV of 0.5% acquired in several hundred milliseconds. (Pritz et al., Expert Opin. Drug Discovery 6, 663 (2011)). If we assume a single 4 ns lifetime and 0.2 ns bins, this measurement would have a peak channel photon count of about 5000 corresponding to an SNR of 70. This is comparable to our performance with no signal averaging (FIG. 14) and at least 5-fold worse than our actual SNR performance in a 0.5 s acquisition. In another example (Paterson et al., Anal. Biochem., 402, 54 (2010)) a 5 MHz TCSPC instrument acquired 10 000 peak channel photon counts in 3 s, an SNR of 100. Increasing SNR to 400 would require ~50 s acquisition in this example. DWR provides SNR of 400 or greater in 200 ms (200 cycles averaged), at least 100-fold faster when compared with TCSPC. The transport time of the microplate stage (0.3 s) limits our plate reader to a per-well acquisition time of 0.5 s (200 cycles averaged). With this limitation, the two methods are roughly comparable in speed.

Several factors affect the per-well acquisition time. Waveform averaging provides some protection against fluctuations in the fluorescence signal on the ms time scale, e.g., due to motion of contaminating particulates. We routinely average 200 waveforms per well. Averaging is not necessary as instrument noise is quite low (~0.5 mV or less) providing high SNR. Reducing the number of waveforms to 50 modestly improves the acquisition time to 0.35 s, but may harm resolution. Similarly, pulse interleaving may be disabled to increase acquisition rate at a cost of decreased resolution of lifetime components. We are currently pursuing a rapid scan mode to decrease acquisition time to 0.1 s per well. Early results show SNR comparable to data acquired with 50 cycles averaged, a 3.5-fold improvement in speed.

Cost is another limitation in high-throughput screening assays. We have used costly glass plates in this study, but have tested plastic plates (polystyrene or cyclic olefin polymer) finding their precision to comparable. Plastic plates generate autofluorescence that hinders lifetime resolution. Assays that do not require resolution of component mole fractions may therefore benefit from plastic plates. We have begun development of a top-read format plate reader that enables use of lower cost polypropylene plates. Early results show comparable precision to that presented here (CV of lifetime better than 0.5%).

Direct waveform recording relies on the linearity of the analog current generated by the PMT. While the total intensity signal of our instrument is linear with excitation power (FIG. 10) and concentration (FIG. 11), nonlinearity results in a correlation of apparent lifetime with intensity. The nonlinearity is likely due to physical limitations in the PMT at high peak output current (2 mA for a 100 mV signal). High intensity signals produce slightly longer lifetimes as a result. The effect is small (~50 ps per fluorescence unit, FIG. 12). We find nonlinearity has negligible effect when intensity varies due to experimental error alone (FIG. 9) as per-well precision (~10 ps) becomes limiting. Assays requiring full dynamic range should consider the effect of nonlinearity on apparent lifetime. This effect is a subject of ongoing study.

Other approaches to improving resolution of fluorescence assays include homogeneous time-resolved fluorescence (HTRF) using long-lived lanthanide probes (Degorce et al., Curr. Chem. Genomics, 3, 22 (2009)) or development of ratiometric assays that exploit changes in emission spectra, for example, the ratio of donor to acceptor emission in a FRET pair. (Meng et al., J. Cell Sci., 125, 743 (2012)). Both of these techniques limit the choice of probes available and do not eliminate the issue of signal precision common to intensity-based measurements. For applications requiring greater sensitivity and rejection of signal interference, enzyme-coupled bioluminescence assays remain the gold standard. (Acker et al., Perspect. Sci., 1, 56 (2014); Inglese et al., Nat. Chem. Biol., 3, 466 (2007)).

Fluorescence lifetime has been pursued for improvement of high-throughput screening assays for many years. The high precision of DWR has enabled development of new types of fluorescence assays including time-resolved transient kinetics (Nesmelov et al., Proc. Natl. Acad. Sci. U.S.A., 108(5), 1891(2011)) and the recently reported time-resolved flow cytometry measurement of single cells (Li et al., Electrophoresis, 35(12-13), 1846(2014)). The lifetime plate reader described here demonstrates that direct waveform recording achieves excellent signal-to-noise and per-well precision while providing fast acquisition rates suitable for drug screening and other high-throughput applications.

The present invention is illustrated by the following examples. It is to be understood that the particular examples, materials, amounts, and procedures are to be interpreted broadly in accordance with the scope and spirit of the invention as set forth herein.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for identifying a compound that alters fluorescence resonance energy transfer (FRET) of a protein comprising:
   providing a genetically engineered cell comprising a target protein,
      wherein the cell is a live cell,
      wherein the target protein comprises two heterologous domains, wherein a first heterologous domain comprises a first chromophore, wherein a second heterologous domain comprises a second chromophore, and wherein each heterologous domain comprises a fluorescent protein;
   contacting the live cell with a test compound to form a mixture;
   measuring the fluorescence lifetime of the first chromophore, the second chromophore, or the combination thereof, of the live cell,
   wherein the measuring comprises use of a plate reader and direct waveform recording of fluorescence lifetime decays,
      wherein the measuring occurs over a period of time no greater than 0.5 seconds;
   calculating a coefficient of variation (CV) for the fluorescence lifetime of the first chromophore, the second chromophore, or the combination thereof, wherein CV is no greater than 0.5%; and
   calculating a Z' parameter, wherein the Z' parameter is >0.5;
      wherein a difference between the fluorescence lifetime in the presence of the test compound and the fluorescence lifetime in the absence of the test compound indicates that the test compound alters the FRET of the target protein.

2. The method of claim 1 wherein the fluorescence lifetime of the first chromophore, the second chromophore, or the combination thereof, is changed in the presence of the test compound.

3. The method of claim 1 adapted for use in a high-throughput format.

4. The method of claim 1 wherein the target protein is stably expressed by the genetically engineered cell.

5. The method of claim 1 wherein the cell is a eukaryotic cell.

6. The method of claim 5 wherein the cell is a vertebrate cell.

7. The method of claim 1 wherein the measuring occurs over a period of time no greater than 0.001 seconds.

8. The method of claim 1 wherein the first chromophore and the second chromophore are selected from a green fluorescent protein, a red fluorescent protein, and a yellow fluorescent protein, or an analogue thereof.

9. The method of claim 1 wherein the cell is in suspension.

10. A method for identifying a compound that alters fluorescence resonance energy transfer (FRET) of a protein comprising:
   providing a genetically engineered cell comprising a target protein and a second protein,
      wherein the cell is a live cell,
      wherein the target protein comprises a first heterologous domain that comprises a first chromophore, and wherein the second protein comprises a second heterologous domain that comprises a second chromophore, and wherein each heterologous domain comprises a fluorescent protein;
   contacting the live cell with a test compound to form a mixture; and
   measuring the fluorescence lifetime of energy emitted by the first chromophore, the second chromophore, or the combination thereof, of the live cell, wherein the measuring comprises use of a plate reader and direct waveform recording of fluorescence lifetime decays,
  wherein the measuring occurs over a period of time no greater than 0.5 seconds;
calculating a coefficient of variation (CV) for the fluorescence lifetime of the first chromophore, the second chromophore, or the combination thereof, wherein the CV is no greater than 0.5%; and
calculating a Z' parameter, wherein the Z' parameter is >0.5;
  wherein a difference between the fluorescence lifetime in the presence of the test compound and the fluorescence lifetime in the absence of the test compound indicates that the test compound alters the FRET of the target protein, the second protein, or the combination thereof.

11. The method of claim 10 wherein the target protein and second protein are stably expressed by the genetically engineered cell.

12. The method of claim 10 wherein the fluorescence lifetime of the first chromophore, the second chromophore, or the combination thereof, is changed in the presence of the test compound.

13. The method of claim 10 adapted for use in a high-throughput format.

14. The method of claim 10 wherein the cell is a eukaryotic cell.

15. The method of claim 14 wherein the cell is a vertebrate cell.

16. The method of claim 10 wherein the measuring occurs over a period of time no greater than 0.001 seconds.

17. The method of claim 10 wherein the first chromophore and the second chromophore are selected from a green fluorescent protein, a red fluorescent protein, and a yellow fluorescent protein, or an analogue thereof.

18. The method of claim 10 wherein the cell is in suspension.

19. The method of claim 1 wherein the target protein is transiently expressed by the genetically engineered cell.

* * * * *

UNITED STATES PATENT AND TRADEMARK OFFICE
CERTIFICATE OF CORRECTION

| | |
|---|---|
| PATENT NO. | : 10,794,898 B2 |
| APPLICATION NO. | : 14/598707 |
| DATED | : October 6, 2020 |
| INVENTOR(S) | : David D. Thomas et al. |

It is certified that error appears in the above-identified patent and that said Letters Patent is hereby corrected as shown below:

On the Title Page

In Lines 13 and 14 of the Abstract, delete "with a compound A difference" and replace with
--with a compound. A difference--

In the Specification

In Column 1, Lines 14-17, delete the entire paragraph and replace with the following paragraph:
--This invention was made with government support under GM27906, AG42996, and HL092097 awarded by the National Institutes of Health. The government has certain rights in the invention. This work was supported by an award from the American Heart Association.--

Signed and Sealed this
Nineteenth Day of January, 2021

Andrei Iancu
*Director of the United States Patent and Trademark Office*